United States Patent
Reategui et al.

(10) Patent No.: US 11,548,002 B2
(45) Date of Patent: Jan. 10, 2023

(54) ENGINEERED NANO-INTERFACES FOR MICROFLUIDIC ISOLATION OF EXTRACELLULAR VESICLES

(71) Applicant: The General Hospital Corporation, Boston, MA (US)

(72) Inventors: Eduardo Reategui, Dublin, OH (US); Shannon Stott, Winchester, MA (US); Mehmet Toner, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 233 days.

(21) Appl. No.: 16/613,710

(22) PCT Filed: May 21, 2018

(86) PCT No.: PCT/US2018/033749
§ 371 (c)(1),
(2) Date: Nov. 14, 2019

(87) PCT Pub. No.: WO2018/213847
PCT Pub. Date: Nov. 22, 2018

(65) Prior Publication Data
US 2020/0070168 A1    Mar. 5, 2020

Related U.S. Application Data

(60) Provisional application No. 62/508,461, filed on May 19, 2017.

(51) Int. Cl.
*B01L 3/00*    (2006.01)
*G01N 33/543*    (2006.01)
(Continued)

(52) U.S. Cl.
CPC ...... *B01L 3/502761* (2013.01); *B01F 25/431* (2022.01); *B01F 33/30* (2022.01);
(Continued)

(58) Field of Classification Search
CPC .. B01L 3/502761; B01L 3/5027; B01L 3/502; B01L 3/50; B01L 2200/0668;
(Continued)

(56) References Cited

U.S. PATENT DOCUMENTS

2011/0166034 A1    7/2011    Kwong et al.
2012/0258475 A1    10/2012    Tang et al.
(Continued)

FOREIGN PATENT DOCUMENTS

WO    WO 2016/023008    2/2016
WO    WO 2016/077067    5/2016
WO    WO 2017/062901    4/2017

OTHER PUBLICATIONS

Abe et al., "Copy Number variation of the antimicrobial-gene, defensin beta 4, is associated with susceptibility to cervical cancer," J. Hum. Genet., May 2013, 58(5):250-253.
(Continued)

*Primary Examiner* — Christine T Mui
(74) *Attorney, Agent, or Firm* — Fish & Richardson P.C.

(57) ABSTRACT

Systems and techniques are described for capturing target extracellular vesicles from a fluid sample. In some implementations, a microfluidic device includes a microfluidic channel where an internal surface of at least one wall of the microfluidic channel includes a plurality of grooves or ridges, or both grooves and ridges, arranged and configured to generate chaotic mixing within a fluid sample flowing through the microfluidic channel. The microfluidic device also includes a plurality of elongate flexible linker molecules, each having a molecular weight between about 1.8-4.8 kDa, where each elongate flexible linker molecule is bound at a first end to an internal surface of at least one wall
(Continued)

of the microfluidic channel and is bound at a second end to one or more binding moieties that specifically bind to a target extracellular vesicle.

16 Claims, 16 Drawing Sheets

(51) Int. Cl.
B01F 25/431 (2022.01)
B01F 33/30 (2022.01)

(52) U.S. Cl.
CPC .. *G01N 33/54313* (2013.01); *B01F 25/43172* (2022.01); *B01F 25/431971* (2022.01); *B01L 2200/0668* (2013.01); *B01L 2300/0636* (2013.01); *B01L 2300/0816* (2013.01); *B01L 2300/0851* (2013.01); *B01L 2400/0487* (2013.01); *B01L 2400/086* (2013.01)

(58) Field of Classification Search
CPC ..... B01L 2300/0636; B01L 2300/0816; B01L 2300/0851; B01L 2400/0487; B01L 2400/086; B01F 5/061; B01F 5/0609; B01F 5/0602; B01F 5/06; B01F 2005/0623; B01F 2005/066; B01F 13/0059; G01N 33/54313
USPC .................................................. 422/502, 500
See application file for complete search history.

(56) References Cited

U.S. PATENT DOCUMENTS

2015/0369804 A1   12/2015  Reategui et al.
2015/0377753 A1*  12/2015  Toner ............... G01N 33/57434
                                                    436/178

OTHER PUBLICATIONS

Alani et al., "Id1 regulation of cellular senescence through transcriptional repression of p16/Ink4a," Proc. Natl. Acad. Sci., Jul. 2001, 98(14):7812-7816.
André et al., "P2Y (12) regulates platelet adhesion/activation, thrombus growth, and thrombus stability in injured arteries," J. Clin. Invest., Aug. 2003, 112(3):398-406.
Baig et al., "Mutational Spectrum of Gelsolin and its Down Regulation is Associated with Breast Cancer," Dis. Markers, Jan. 2013, 34(2):71-80.
Barbazan et al., "Prognostic Impact of Modulators of G proteins in Circulating Tumor Cells from Patients with Metastatic Colorectal Cancer," Scientific Reports, Feb. 2016, 6(1):22112.
Beaufort et al., "Cerebral small vessel disease-related protease HtrA1 processes latent TGF-β binding protein 1 and facilitates TGF-β signaling," Proceedings of the National Academy of Sciences, Nov. 2014, 111(46):16496-16501.
Boom et al., "Identification of novel genes associated with astrocytoma progression using suppression subtractive hybridization and real-time reverse transcription-polymerase chain reaction," Int. J. Cancer, Nov. 2006, 119(10):2330-2338.
Cancerres.aacrjournals.org [online], "Abstract 5000: Upregulation of WDR26 promotes breast cancer cell growth, migration and invasion via enhancing PI3K/AKT signaling," Oct. 2014, retrieved on Sep. 2, 2020, retrieved from URL<https://cancerres.aacrjournals.org/content/74/19_Supplement/5000>, 4 pages.
Candido et al., "Roles of NGAL and MMP-9 in the tumor microenvironment and sensitivity to targeted therapy," Biochimica et Biophysica Acta (BBA)—Molecular Cell Research, Mar. 2016, 1863(3):438-448.
Cervelli et al., "Spermine oxidase (SMO) activity in breast tumor tissues and biochemical analysis of the anticancer spermine analogues BENSpm and CPENSpm," BMC Cancer, Dec. 2010, 10(1):555, 10 pages.
Checquolo et al., "Differential subcellular localization regulates c-Cbl E3 ligase activity upon Notch3 protein in T-cell leukemia," Oncogene, Mar. 2010, 29(10):1463-1474.
Chen & Geng, "P-selectin mediates adhesion of leukocytes, platelets, and cancer cells in inflammation, thrombosis, and cancer growth and metastasis," archivum Immunologiae et Therapiae Experimentalsis, Apr. 2006, 54(2):75-84.
Choudhury et al., "Attenuated adenosine-to-inosine editing of microRNA-376a promotes invasiveness of glioblastoma cells," The Journal of Clinical Investigation, Nov. 2012, 122(11):4059-4076.
Cools et al., "Fusion of a Novel Gene, BTL, to ETV6 in Acute Myeloid Leukemias With a t(4;12)(q11-q12;p13)," Blood, Sep. 1999, 94(5):1820-1824.
Currie et al., "Cellular Fatty Acid Metabolism and Cancer," Cell Metabolism, Aug. 2013, 18(2):153-161.
Devkota et al., "Ei24-deficiency attenuates protein kinase Cα signaling and skin carcinogenesis in mice," The International Journal of Biochemistry & Cell Biology, Nov. 2012, 44(11):1887-1896.
Ding et al., "The Histone H3 Methyltransferase G9A Epigenetically Activates the Serine-Glycine Synthesis Pathway to Sustain Cancer Cell Survival and Proliferation," Cell Metabolism, Dec. 2013, 18(6):896-907.
Ensign et al., "Implications of Rho GTPase Signaling in Glioma Cell Invasion and Tumor Progression," Frontiers in Oncology, Oct. 2013, 3:241-241.
Fang et al., "The SOX2 response program in glioblastoma multiforme: an integrated ChIP-seq, expression microarray, and microRNA analysis," BMC Genomics, Dec. 2011, 12(11), 17 pages.
Friedman et al., "C8orf4 is a transforming growth factor B induced transcript downregulated in metastatic colon cancer," Int. J. Cancer, Aug. 2004, 111(1):72-75.
Galeano et al., "ADAR2-editing activity inhibits glioblastoma growth through the modulation of the CDC14B/Skp2/p21/p27 axis," Oncogene, Feb. 2013, 32(8):998-1009.
Gallia et al., "PIK3CA Gene Mutations in Pediatric and Adult Glioblastoma Multiforme," Mol. Cancer Res., Oct. 2006, 4(10):709-714.
GenBank Accession No. NG_009364.1, *Homo sapiens* cyclin dependent kinase inhibitor 1A (CDKN1A), RefSeqGene on chromosome 6, May 24, 2020, 7 pages.
GenBank Accession No. NM_004357.4, "*Homo sapiens* CD151 molecule (Raph blood group) (CD151), transcript variant 1, mRNA," Nov. 11, 2018, 5 page.
Goodsell, "The Molecular Perspective: The *ras* Oncogene," Stem Cells, Jul. 1999, 17(4):235-236.
Goodwin et al., "Increased Spermine Oxidase Expression in Human Prostate Cancer and Prostatic Intraepithelial Neoplasia Tissues," The Prostate, May 2008, 68(7):766-772.
Goriounov et al., "Protein products of human related genes on chromosomes 17 and 22 associate with both microfilaments and microtubules," J. Cell Sci., Mar. 2003, 116(6):1045-1058.
Gu et al., "Association of endothelin-converting enzyme-1b C-338A polymorphism with gastric cancer risk: A case-control study," Eur. J. Cancer, Jun. 2008, 44(9):4253-1258.
Guinn et al., "Humoral detection of leukemia-associated antigens in presentation acute myeloid leukaemia," Biochem. Biophys. Res. Commun., Oct. 2005, 335(4):4293-1304.
Heyn & Esteller., "DNA methylation profiling in the clinic: applications and challenges," Nat. Rev. Genet., Oct. 2012, 13(10):679-692.
Hollstein & Cichowski, "Identifying the ubiquitin ligase complex that regulates the NF1 tumor suppressor and Ras," Cancer Discovery, Aug. 2013, 3(8):880-893.
Hsu et al., "IKKε coordinates invasion and metastasis of ovarian cancer," Cancer Res., Nov. 2012, 72(21):5494-5504.
Huang et al., "Membrane Transporters and Channels: Role of the Transportome in Cancer Chemosensitivity and Chemoresistance,"Cancer Research, Jun. 2004, 64(12):4294-4301.

(56) References Cited

OTHER PUBLICATIONS

Hutti et al., "Phosphorylation of the tumor suppressor CYLD by the breast cancer oncogene IKKε promotes cell transformation," Mol. Cell., May 2009, 34(4):461-472.
Ishiyama et al., "OCIA domain containing 2 is highly expressed in adenocarcinoma mixed subtype with bronchioloalveolar carcinoma component and is associated with better prognosis," Cancer Sci., Jan. 2007, 98(1):50-57.
Itkonen et al., "UAP1 is overexpressed in prostate cancer and is protective against inhibitors of N-linked glycosylation," Oncogene, Jul. 2015, 34(28):3744-3750.
Ito et al., "Uroporphyrinogen Decarboxylase is a Radiosensitizing Target for Head and Neck Cancer," Sci. Transl. Med., Jan. 2011, 3(67):67ra67-67ra67.
Jakobsen et al., "Novel asymmetrically localizing components of human centrosomes identified by complementary proteomics methods," The EMBO Journal, Apr. 2011, 30(8):4520-1535.
Kanojia et al., "Genomic landscape of liposarcoma," Oncotarget, Dec. 2015, 6(40):42429-42444.
Karnati et al., "Down Regulated Expression of Claudin-1 and Claudin-5 and Up Regulation of β-catenin: association with human glioma progression," CNS & Neurological Disorders—Drug Targets, Oct. 2014, 13(8):4413-1426.
Kauppila et al., "Toll-like receptor 5 (TLR5) expression is a novel predictive marker for recurrence and survival in squamous cell carcinoma of the tongue," Br. J. Cancer, Feb. 2013, 108(3):638-643.
Kehlen et al., "Role of glutaminyl cyclases in thyroid carcinomas," Endocrine-Related Cancer, Feb. 2013, 20(1):79-90.
Kim et al., "CRL4A-FBXW5-mediated degradation of DLC1 Rho GTPase-activating protein tumor suppressor promotes non-small cell lung cancer cell growth," Proceedings of the National Academy of Sciences of the United States of America, Oct. 2013, 110(42):46868-16873.
Kim et al., "Pro-apoptotic role of integrin β3 in glioma cells," J. Neurochem, May 2011, 117(3):494-503.
Kim et al., "TC1 (C8orf4) Correlates with Wnt/β-Catenin Target Genes and Aggressive Biological Behavior in Gastric Cancer," Clin. Cancer. Res., Jun. 2006, 12(11):3541-3548.
King & Bertram., "Connexins as targets for cancer chemoprevention and chemotherapy," Biochimica et Biophysica Acta (BBA)—Biomembranes, Dec. 2005, 1719(1-2):146-160.
Korošec et al., "ATP2A3 gene is involved in cancer susceptibility," Cancer Genet. Cytogenet., Jan. 2009, 188(2):88-94.
Kunita et al., "Identification and Characterization of Novel Members of the CREG Family, Putative Secreted Glycoproteins Expressed Specifically in Brain," Genomics, Nov. 2002, 80(5):456-460.
Lai et al., "DEPTOR Expression Negatively Correlates with mTORC1 Activity and Tumor Progression in Colorectal Cancer. Asian Pacific Journal of Cancer Prevention," Jan. 2014, 15(11):4589-4594.
Latha et al., "Nuclear EGFRvIII-STAT5b complex contributes to glioblastoma cell survival by direct activation of the Bc1-XL promoter," International Journal of Cancer, Feb. 2013, 132(3):509-520.
Lauriat et al., "Characterization of KIAA0513, a novel signaling molecule that interacts with modulators of neuroplasticity, apoptosis, and the cytoskeleton," Brain Res., Nov. 2006, 1121(1):1-11.
Lee et al., "Prognostic significance of tetraspanin CD151 in newly diagnosed glioblastomas," Journal of Surgical Oncology, May 2013, 107(6):646-652.
Lei et al., "TC-1 Overexpression Promotes Cell Proliferation in Human Non-Small Cell Lung Cancer that Can Be Inhibited by PD173074," PloS One, Jun. 2014, 9(6):e100075, 11 pages.
Li et al., "DEPTOR has growth suppression activity against pancreatic cancer cells," Oncotarget, Dec. 2014, 5(24):12811-12819.
Li et al., "IKBKE Upregulation is Positively Associated with Squamous Cell Carcinoma of the Lung in Vivo and Malignant Transformation of Human Bronchial Epithelial Cells in Vitro," Medical Science Monitor : International Medical Journal of Experimental and Clinical Research, May 2015, 21:1577-1586.
Li et al., "SSX2IP promotes metastasis and chemotherapeutic resistance of hepatocellular carcinoma," J. Transl. Med., Dec. 2013, 11(1):52.
Liebermann & Hoffman, "Gadd45 in stress signaling," Journal of Molecular Signaling, Sep. 2008, 3:15, 8 pages.
Liu et al., "Concurrent Down-regulation of Egr-1 and Gelsolin in the Majority of Human Breast Cancer Cells," Cancer Genomics—Proteomics, Nov. 2007, 4(6):377-385.
Loilome et al., "PRKAR1A is overexpressed and represents a possible therapeutic target in human cholangiocarcinoma," Int. J. Cancer, Jul. 2011, 129(1):34-44.
Lomakina et al., "Arpin downregulation in breast cancer is associated with poor prognosis," Br. J. Cancer., Mar. 2016, 114(5):545-553.
Lou et al., "MFAP3L activation promotes colorectal cancer cell invasion and metastasis," Biochimica et Biophysica Acta (BBA)—Molecular Basis of Disease, Sep. 2014, 1842(9):1423-1432.
Lv et al., "DEDD Interacts with PI3KC3 to Activate Autophagy and Attenuate Epithelial—Mesenchymal Transition in Human Breast Cancer," Cancer Res. Jul. 2012, 72(13):3238-3250.
Lysenko et al. "BACL is a Novel Brain-Associated, Non-NKC-Encoded Mammalian C-Type Lectin-Like Receptor of the CLEC2 Family," PloS One, Jun. 2013, 8(6):e65345, 14 pages.
Meng et al., "A radiosensitivity gene signature in predicting glioma prognostic via EMT pathway," Oncotarget, Jul. 2014, 5(13):4683-4693.
Merkley et al., "2D-DIGE proteomic characterization of head and neck squamous cell carcinoma," Otolaryngology—Head and Neck Surgery, Nov. 2009, 141(5):626-632.
Milinkovic et al., "Identification of Novel Genetic Alterations in Samples of Malignant Glioma Patients," PloS One, Dec. 2013, 8(12):e82108, 11 pages.
Nagata et al., "Increased expression of OCIA domain containing 2 during stepwise progression of ovarian mucinous tumor," Pathology International, Jul. 2012, 62(7):471-476.
Nair et al., "Gene and miRNA expression changes in squamous cell carcinoma of larynx and hypopharynx," Genes & Cancer, Jul. 2015, 6(7-8):328-340.
Ni et al., "The Ubiquitin-Proteasome Pathway Mediates Gelsolin Protein Downregulation in Pancreatic Cancer," Molecular Medicine, Sep. 2008, 14(9):582-589.
Niemczyk et al., "Imprinted Chromatin around DIRAS3 Regulates Alternative Splicing of GNG12-AS1, a Long Noncoding RNA," Am. J. Hum. Genet., Aug. 2013, 93(2):224-235.
Noushmehr et al., "Identification of a CpG Island Methylator Phenotype that Defines a Distinct Subgroup of Glioma," Cancer Cell, May 2010, 17(5):510-522.
Park et al., "AF1q is a novel TCF7 co-factor which activates CD44 and promotes breast cancer metastasis," Oncotarget, Aug. 2015, 6(24):20697-20710.
Parvani et al., "Deptor Enhances Triple-Negative Breast Cancer Metastasis and Chemoresistance through Coupling to Survivin Expression," Neoplasia, Mar. 2015, 17(3):317-328.
PCT International Preliminary Report on Patentability in PCT Appln. No. PCT/US2018/033749, dated Nov. 29, 2019, 11 pages.
PCT International Search Report and Written Opinion in International Appln. No. PCT/US2018/033749, dated Jul. 27, 2018, 19 pages.
Péant et al., "IκB-Kinase-ε (IKKε/IKKi/IκBKε) expression and localization in prostate cancer tissues," The Prostate, Jul. 2011, 71(10):1131-1138.
Pei et al., "Overexpression of DEP domain containing mTOR-interacting protein correlates with poor prognosis in differentiated thyroid carcinoma," Molecular Medicine Reports, Sep. 2011, 4(5):817-823.
Peterson et al., "DEPTOR is an mTOR Inhibitor Frequently Overexpressed in Multiple Myeloma Cells and Required for Their Survival," Cell, May 2009, 137(5):873-886.
Pfirschke et al., "Common TLR5 Mutations Control Cancer Progression," Cancer Cell, Jan. 2015, 27(1):1-3.
Pibouin et al., "Cloning of the mRNA of overexpression in colon carcinoma-1: a sequence overexpressed in a subset of colon carcinomas," Cancer Genet. Cytogenet., Feb. 2002, 133(1):55-60.

(56) References Cited

OTHER PUBLICATIONS

Puri et al., "Mast Cell Degranulation Requires N-Ethylmaleimide-Sensitive Factor-Mediated SNARE Disassembly," The Journal of Immunology, Nov. 2003, 171(10):5345-5352.
Qin et al., "The Transcription Factors Sp1, Sp3, and AP-2 Are Required for Constitutive Matrix Metalloproteinase-2 Gene Expression in Astroglioma Cells," J. Biol. Chem., Oct. 1999, 274(41):29130-29137.
Ren et al., "Phyllodes tumor of the breast: role of Axl and ST6GalNAcII in the development of mammary phyllodes tumors," Tumor Biol., Oct. 2014, 35(10):9603-9612.
Saino et al., "Inhibition of angiogenesis in human glioma cell lines by antisense RNA from the soluble guanylate cyclase genes, GUCY1A3 and GUCY1B3," Oncol. Rep., Jul. 2004, 12(1):47-52.
Santos & Schulze, "Lipid metabolism in cancer," FEBS J., Aug. 2012, 279(15):2610-2623.
Scanlan et al., "Antigens recognized by autologous antibody in patients with renal-cell carcinoma," Int. J. Cancer, Nov. 1999, 83(4):456-464.
Semlali et al., "Expression and New Exon Mutations of the Human Beta Defensins and Their Association on Colon Cancer Development," PloS One, Jun. 2015, 10(6):e0126868, 16 pages.
Shalata et al., "Morbid Obesity Resulting from Inactivation of the Ciliary Protein CEP19 in Humans and Mice," Am. J. Hum. Genet, Dec. 2013, 93(6):1061-1071.
Shields et al., "RBBP9: A tumor-associated serine hydrolase activity required for pancreatic neoplasia," Proceedings of the National Academy of Sciences, Feb. 2010, 107(5):2189-2194.
Smollich et al., "On the role of endothelin-converting enzyme-1 (ECE-1) and neprilysin in human breast cancer," Breast Cancer Research, Dec. 2007, 106(3):361-369.
Steffen et al., "MT1-MMP-Dependent Invasion is Regulated by TI-VAMP/VAMP7," Curr. Biol., Jun. 2008, 18(12):926-931.
Sunde et al., "TC-1 is a Novel Tumorigenic and Natively Disordered Protein Associated with Thyroid Cancer," Cancer Res., Apr. 2004, 64(8):2766-2773.
Tseng et al., "Interaction of an Intracellular Pentraxin with a BTB-Kelch Protein is Associated with Ubiquitylation, Aggregation and Neuronal Apoptosis," Molecular and Cellular Neurosciences, Aug. 2011, 47(4):254-264.
Türeci et al., "The SSX-2 Gene, Which is Involved in the t(X;18) Translocation of Synovial Sarcomas, Codes for the Human Tumor Antigen HOM-MEL-40," Cancer Res., Oct. 1996, 56(20):4766-4772.
Valiente et al., "Binding of PTEN to Specific PDZ Domains Contributes to PTEN Protein Stability and Phosphorylation by Microtubule-associated Serine/Threonine Kinases,". J. Biol. Chem., Aug. 2005, 280(32):28936-28943.
Verderio et al., "TI-VAMP/VAMP7 is the SNARE of secretory lysosomes contributing to ATP secretion from astrocytesl," Biol, Cell., Apr. 2012, 104(4):213-228.
Walter et al., "DNA Methylation Profiling Defines Clinically Relevant Biological Subsets of Non-Small Cell Lung Cancer," Clin. Cancer. Res., Apr. 2012, 18(8):2360-2373.
Wee et al., "Selective Calcium Sensitivity in Immature Glioma Cancer Stem Cells," PloS One, Dec. 2014, 9(12):e115698.
Whyteside et al., "ECE-1 influences prostate cancer cell invasion via ET-1-mediated FAK phosphorylation and ET-1-independent mechanisms," Canadian Journal of Physiology and Pharmacology, Aug. 2010, 88(8):850-854.
Williams et al., "SNAP23, Syntaxin4, and vesicle-associated membrane protein 7 (VAMP7) mediate trafficking of membrane type 1-matrix metalloproteinase (MT1-MMP) during invadopodium formation and tumor cell invasion," Molecular Biology of the Cells, Jul. 2014, 25(13):2061-2070.
Wit et al., "LRRTM2 Interacts with Neurexin1 and Regulates Excitatory Synapse Formation," Neuron, Dec. 2009, 64(6):799-806.
Wong et al., "PRKAR1B mutation associated with a new neurodegenerative disorder with unique pathology," Brain, May 2014, 137(5):1361-1373.
Wu et al., "Up-regulation of Anxa2 gene promotes proliferation and invasion of breast cancer MCF-7 cells," Cell Proliferation, Jun. 2012, 45(3):189-198.
Xu et al., "Roles of CXCL5 on migration and invasion of liver cancer cells," J. Transl. Med., Dec. 2014, 12(1):1-11.
Xu et al., "TC-1 (C8orf4) expression is correlated with differentiation in ovarian carcinomas and might distinguish metastatic ovarian from metastatic colorectal carcinomas," Virchows Archiv., Mar. 2013, 462(3):281-287.
Yang et al., "Transforming properties of TC-1 in human breast cancer: Interaction with FGFR2 and β-catenin signaling pathways," Int. J. Cancer, Sep. 2007, 121(6):1265-1273.
Ye et al., "Upregulated WDR26 serves as a scaffold to coordinate PI3K/ Akt pathway-driven breast cancer cell growth, migration, and invasion," Oncotarget, Apr. 2016, 7(14):17854-17869.
Ying et al., "Cloning and Characterization of F-LANa, Upregulated in Human Liver Cancer," Biochem. Biophys. Res. Commun., Aug. 2001, 286(2):394-400.
Yoshida et al., "STX11 functions as a novel tumor suppressor gene in peripheral T-cell lymphomas," Cancer Sci., Oct. 2015, 106(10):1455-1462.
Zhang & Dou., "PCBP1 is an important mediator of TGF-β-induced epithelial to mesenchymal transition in all bladder cancer cell line GBC-SD," Mol. Biol. Rep., Aug. 2014, 41(8):5519-5524.
Zhang et al., "MicroRNA-195 plays a tumor-suppressor role in human glioblastoma cells by targeting signaling pathways involved in cellular proliferation and invasion," Neuro-Oncology, Mar. 2012, 14(3):278-287.
Zhao et al., "Annexin II promotes invasion and migration of human hepatocellular carcinoma cells in vitro via its interaction with HAb18G/CD 147," Cancer Sci., Feb. 2010, 101(2):387-395.
Zhou et al., "Expression of TLR5 in Different Types of Non-small Cell Lung Cancer Cell Lines and its Activation Mechanism," Chinese Journal of Lung Cancer, Dec. 2014, 18(1):8-15.
Zhou et al., "IRAK-M mediates Toll-like receptor/IL-1R-induced NFκB activation and cytokine production," The EMBO Journal, Feb. 2013, 32(4):583-596.
EP Extended European Search Report in European Appln. No. 18801380.9, dated Feb. 5, 2021, 7 pages.
Li et al., "Biodegradable nano-films for capture and non-invasive release of circulating tumor cells," Biomaterials, 2015, 65:93-102.
Reategui et al., "Engineered nanointerfaces for microfluidic isolation and molecular profiling of tumor-specific extracellular vesicles," Nature Communications, 2018, 9:175, 11 pages.
Reategui et al., "Supporting Information: Tunable Nanostructured Coating for the Capture and Selective Release of Viable Circulating Tumor Cells," Advanced Materials, 2015, 27(9):1593-1599.
Chen et al., "Characterization of Tumor Suppressive Function of comulin in Esophageal Squamous Cell Carcinoma," PloS One, Jul. 2013, 8(7):e68838.
Chen et al., "Poly r(C) Binding Protein-1 is Central to Maintenance of Cancer Stem Cells in Prostate Cancer Cells," Cellular Physiology and Biochemistry, Feb. 2015, 35(3):1052-1061.
Plebani et al., "Long-range Transcriptome Sequencing Reveals Cancer Cell Growth Regulatory Chimeric mRNA," Neoplasia, Nov. 2012, 14(11):1087-1096.
Wygledowska-Kania et al., "Defensin DEFB4A transcript level in the differentiation of keratoacanthoma, squamous and basal cell carcinomas," Postepy Nauk Medycznych, Mar. 2015, 3:159-165.

* cited by examiner

ENGINEERED NANO-INTERFACES FOR MICROFLUIDIC ISOLATION OF EXTRACELLULAR VESICLES

CROSS-REFERENCE TO RELATED APPLICATIONS

This application is a 371 U.S. National Phase Application of PCT/US2018/033749, filed on May 21, 2018, which claims priority to U.S. Provisional Patent Application Ser. No. 62/508,461, filed on May 19, 2017. The contents of the provisional application are incorporated herein by reference in its entirety.

FIELD OF THE INVENTION

This disclosure relates to microfluidic isolation of extracellular vesicles.

BACKGROUND

Extracellular vesicles (EVs) are nanosized, membrane-bound vesicles that are released from cells and typically contain messenger ribonucleic acids (mRNAs), microRNAs, other non-coding RNAs, deoxyribonucleic acids (DNAs), proteins, and lipids, and can server as endogenous delivery vehicles for cell-to-cell communication. Different EV types include microvesicles (MVs), exosomes, oncosomes, and apoptotic bodies. MVs bud from the plasma membrane, are about 100 nm to 1 μm in diameter, and contain cytoplasmic cargo. Exosomes are formed by the fusion of multivesicular bodies with the plasma membrane and have diameters of about 40 to 120 nm. Oncosomes are large EVs (about 1 to about 10 μm in diameter) generated from membrane protrusions, which are produced primarily by malignant cells. Dying cells release vesicular apoptotic bodies (about 50 nm to about 2 μm in diameter) that are typically more plentiful in the body than exosomes or MVs and can vary in content between different biofluids.

Tumorigenesis can affect many pathways that regulate the production of EVs and often results in an increased production of EVs by some tumor cells in comparison to normal cells. These tumor-derived EVs often contain a select subset of proteins and nucleic acids that can manipulate their cellular microenvironments at local and distant sites to promote angiogenesis, invasiveness, and metastasis. For example, cancer patients frequently show increased concentrations of EVs in their circulation, which allows the use of isolated EVs from biofluids as biomarkers for diagnostics and disease monitoring in a non-invasive manner.

SUMMARY

The present disclosure features microfluidic system and methods to perform isolation and molecular profiling of specific "target" EVs, such as tumor-derived EVs. The systems and methods disclosed herein can be used to perform target, e.g., tumor-derived, EV isolation with high specificity (e.g., approximately 94%) within a relatively short time period (e.g., 3 hours or less). The systems can include a microfluidic device with channels (e.g., "microchannels") with one or more surfaces that are coated with binding moieties, e.g., antibodies, to capture target EVs selectively from a fluid sample (e.g., human serum or plasma). The channels can include herringbone grooves that maximize EV interactions with tumor-specific antibodies that are immobilized on a surface of an inner wall of the channels. In some instances, target EVs that are captured in the microfluidic device can be released to enable downstream characterization and functional studies.

Various surface immobilization techniques can be used to improve target-specific capture sensitivity with respect to different sized cells. For example, in the new methods and systems described herein, elongated linker molecules, e.g., flexible linker molecules, of a specified length and/or molecular weight, are immobilized on the substrate, e.g., a nanostructured substrate, to improve capture efficiency for target EVs. As discussed herein, the length of the elongated linker molecules can be used to maximize capture efficiency of EVs from a fluid sample using the microfluidic devices.

In one general aspect, the present disclosure describes a microfluidic device. The microfluidic device includes a microfluidic channel where an internal surface of at least one wall of the microfluidic channel includes a plurality of grooves or ridges, or both grooves and ridges, arranged and configured to generate chaotic mixing within a fluid sample flowing through the microfluidic channel. The microfluidic device also includes a plurality of elongate flexible linker molecules, each having a molecular weight between about 1.8-4.8 kDa, where each elongate flexible linker molecule is bound at a first end to an internal surface of at least one wall of the microfluidic channel and is bound at a second end to one or more binding moieties that specifically bind to a target extracellular vesicle.

One or more implementations can include the following optional features. For example, in some implementations, the microfluidic device includes one or more layers of gelatin. A first layer of the gelatin is bound to the internal surface of the microfluidic channel by physical adsorption or by binding to second members of the binding pair attached to the internal surface or attached to first members of the binding pair attached to the internal surface. An optional second layer of gelatin is bound to the first layer via a plurality of second members of the binding pair that are associated with the first members of the binding pair on both the first and the second layers of gelatin. Optionally, one or more subsequent layers of gelatin, each bound to a previous layer by the second members of the binding pair.

In some implementations, the elongate flexible linkers include at a first end thereof a binding moiety that binds to a surface layer of the gelatin, thus indirectly binding the elongate flexible linkers to the internal surface of the wall via the one or more layers of gelatin.

In some implementations, the microfluidic device includes a plurality of nanostructures. The nanostructures include one or more binding moieties that bind to the internal surface of at least one wall of the microfluidic channel. The elongate flexible linkers are indirectly bound to the internal surface of the wall by an interaction of the first end of the plurality of elongate flexible linker molecules with the nanostructures bound to the internal surface.

In some implementations, the microfluidic device includes a plurality of nanostructures. The nanostructures include one or more binding moieties that bind to a surface layer of the gelatin. The elongate flexible linkers are indirectly bound to the internal surface of the wall by an interaction of the first end of the plurality of elongate flexible linker molecules with the nanostructures bound to the surface layer of gelatin.

In some implementations, the microfluidic device includes a plurality of nanostructures. The nanostructures are bound to a surface layer of gelatin by the second members of the binding pair that are associated with the first members of the binding pair. The elongate flexible linkers are indirectly bound to the internal surface of the wall by an interaction of the first end of the plurality of elongate flexible linker molecules with the nanostructures bound to the surface layer of gelatin.

In some implementations, the plurality of layers of gelatin include at least a first layer of gelatin bound to the internal surface of at least one wall of the microfluidic channel, and a second layer of gelatin bound to the first layer of gelatin via the second members of the binding pair.

In some implementations, the plurality of elongate flexible linker molecules include polyethylene glycol (PEG).

In some implementations, the plurality of elongate flexible linker molecules include dextran.

In some implementations, the one or more binding moieties include at least one of antibodies, aptamers, lectins, heparin, glycoproteins, or deoxyribonucleic (DNA) fragments.

In some implementations, the one or more binding moieties specifically bind to at least one of an epidermal growth factor receptor (EGFR), podoplanin, barrier-to-autointegration factor (BAF), platelet-derived growth factor receptor (PDGFR), and ephrin receptor A2 (EphA2).

In some implementations, the binding moieties specifically bind to tumor-derived extracellular vesicles.

In some implementations, the plurality of grooves or ridges includes two or more V-shaped grooves that are each defined in the least one wall of the microfluidic channel. Each V-shaped groove comprises an apex and two arms connected to the apex to form the V-shape; and the two or more V-shaped grooves each comprise a first V-shaped groove that is orientated such that the apex of the first V-shaped groove points in the direction of flow through the microchannel, and a second V-shaped groove that is oriented such that the apex of the second V-shaped groove points against the direction of flow through the microchannel.

In another general aspect, the present disclosure describes a method of capturing target extracellular vesicles from a fluid sample. The method includes obtaining a substrate having attached to a surface thereof a plurality of elongate flexible linker molecules, each having a molecular weight between about 1.8-4.8 kDa. Each elongate flexible linker molecule is bound at a first end to the surface and is bound at a second end to one or more binding moieties that specifically bind to a target extracellular vesicles. The method also includes flowing the fluid sample through the channel at a flow rate that enables specific binding of the target extracellular vesicles to the binding moieties, thereby capturing the target extracellular vesicles.

One or more implementations can include the following optional features. For example, in some implementations, the substrate includes a microfluidic channel. An internal surface of at least one wall of the microfluidic channel includes a plurality of grooves or ridges, or both grooves and ridges, arranged and configured to generate chaotic mixing within a fluid sample flowing through the microfluidic channel.

In some implementations, the substrate further includes one or more layers of gelatin bound to the surface of the substrate. Additionally, the method further includes releasing the bound target extracellular vesicles from the substrate by separating the one or more layers of gelatin from the substrate.

In some implementations, separating the one or more layers of gelatin from the substrate includes melting, at an increased temperature, the one or more layers of gelatin.

In some implementations, the increased temperature is 37° C.

In some implementations, separating the one or more layers of gelatin from the substrate includes applying a localized shear stress to one or more of the layers of gelatin.

In some implementations, applying the localized shear stress to one or more of the layers of gelatin includes applying a frequency-controlled force to at least a top layer of gelatin.

In another general aspect, the present disclosure describes a method of capturing target extracellular vesicles from a fluid sample. The method includes flowing the fluid sample through a depletion module to remove at least some non-target extracellular vesicles and flowing the fluid sample that exits the depletion module into a capture module. The capture module includes a microfluidic channel where an internal surface of at least one wall of the microfluidic channel comprises a plurality of grooves or ridges, or both grooves and ridges, arranged and configured to generate chaotic mixing within a fluid sample flowing through the microfluidic channel. The capture module also includes a plurality of elongate flexible linker molecules, each having a molecular weight between about 1.8-4.8 kDa, where each elongate flexible linker molecule is bound at a first end to an internal surface of at least one wall of the microfluidic channel and is bound at a second end to one or more binding moieties that specifically bind to a target extracellular vesicle. The target extracellular vesicles are captured in the capture module.

In some implementations, the method further includes isolating biological cargo from the extracellular vesicles and analyzing the biological cargo.

In some implementations, the biological cargo comprises at least one of deoxyribonucleic acid (DNA), ribonucleic acid (RNA), proteins, lipids, and cytokines.

In some implementations, the depletion module includes a microfluidic channel. An internal surface of at least one wall of the microfluidic channel of the depletion module includes a plurality of grooves or ridges, or both grooves and ridges, arranged and configured to generate chaotic mixing within a fluid sample flowing through the microfluidic channel of the depletion module. Non-target extracellular vesicles are captured in the depletion module.

The systems and techniques disclosed herein can be used to address many limitations in prior technologies for EV isolation and capture from a fluid sample that often prevent EVs from being widely used in clinical settings. For instance, many EV isolation technologies often rely on techniques (e.g., ultracentrifugation, precipitation processing) that rely on EV physical properties for isolation. However, these techniques often isolate not only target EVs, such as tumor-derived EVs, but also non-target EVs derived from non-malignant cells such as platelets, endothelial cells, and immunological cells. This often yields low throughput outcomes and low specificity. While antibody-coated bead-based assays can be used to improve specific isolation of tumor-derived EVs, these assays often take a relatively long time to complete and can consist of multiple labeling steps. Such assays are also typically not very efficient, as the interactions between the antibody coated beads and EVs are statistically challenging to optimize and can also suffer from steric hindrance effects and could benefit from use of flexible linker molecules as discussed in detail below.

Moreover, the systems and techniques disclosed herein provide various advantages over other types of microfluidic particle capture systems. For example, a deterministic lateral displacement (DLD) technique can be used to sort populations of small nanometer EVs from micrometer-size particles. While a nano-DLD device can achieve a sorting resolution that allows separation between 10 nm to 110 nm populations of exosomes, techniques using the device often lack specificity towards tumor-derived EVs and may miss detection of important biological cargo. Other approaches include the use of plasmonic sensor devices that can immobilize and then quantify EVs. However, these devices are complicated to manufacture and scale up, and usually, operate at low throughput.

In addition, the microfluidic systems described herein provide improved specificity for capturing target EVs. The target EVs can be captured in channels of microfluidic devices that are coated with surface chemistry specific to the target EVs. As discussed in detail below, the surface chemistry, in some implementations, includes multiple layers of gelatin bonded to the channel surface, nanostructured substrates attached to a top layer of gelatin, and multiple elongated flexible linker molecules, e.g., fixed-length polyethylene glycol (PEG) linkers, attached to the nanostructured substrates. The addition of the multiple elongated flexible linker molecules enables improve capture of target EVs compared to, for instance, larger sized cells having 10-20 μm diameters.

The systems and techniques disclosed herein can also sufficiently distinguish between EVs produced by normal and target cells, such as tumor cells, at high throughputs to allow testing with large volumes of serum or plasma (e.g., 3 to 5 mL). In particular implementations, the systems disclosed herein can be used to capture and isolate tumor-derived EVs from fluid samples of GBM patients. In such implementations, the systems can be used for detection of low abundance molecular signatures of mRNAs, such as EGFRvIII, which has 15% to 20% frequency in GBM patients. The systems can be configured to perform EV isolation without requiring enrichment using anti-tetraspanins markers, which often produces undetermined and low tumor-derived EV enrichment ratios. In this regard, the system disclosed herein can be used for the isolation, capture, and investigation of tumor-derived EVs as disease-specific biomarkers for diagnostic purposes.

The systems also enable the simple and easy release of captured target EVs from the surface of microfluidic devices in a manner that preserves biological cargo contents of the captured target EVs. For example, in some instances, the system can extract up to approximately 87% of target EVs that are captured on the microfluidic device. The extracted target EVs can analyzed using downstream processing for clinical investigation. As an example, the extracted target EVs can be investigated for pre-metastatic niche formation since EVs from cancer cells of a primary tumor can remotely prepare distant sites for the spread of tumors in an organ-specific manner. As another example, once isolated and extracted, the target EVs can be studied to determine oncogenic transfer potential to other cells, since many tumor-derived EVs are capable of inducing phenotype changes in surrounding cells.

In some implementations, the systems disclosed herein can be configured to capture EVs of different sizes and are thereby capable of isolating exosomes, microvesicles, and oncosomes that could have significant biological implications with different cargo packaged in EVs based on their mode of biogenesis.

Moreover, the systems can provide improvements to downstream imaging of target EVs due to the increased sensitivity for capturing target EVs. For example, imaging benefits can be correlated to total RNA yield from EVs that can then facilitate the process of optimization for other types of cancer.

As used herein, "functionalizing" a material or a "functionalized" material refers to a modification, e.g., chemical modification, of the material to alter the reactivity of the material. Similarly, functionalizing a surface or a functionalized surface refers to the chemical modification of the surface to alter the reactivity of the surface. For example, the material can be chemically modified by oxidizing, reducing, aminating, or carboxylating one or more chemical functional groups. Functionalizing the surface can include, for example, contacting the surface (e.g., glass) with a chemical compound that introduces amine moieties to the surface. Functionalizing can be performed in one or more chemical reaction steps. A material can be functionalized by reactive contact with one or more functionalizing agents, which can be one or more chemical compounds that react with at least a portion of the hydrogel. For example, biotin-NHS can be bound to primary amines on a gelatin.

As used herein, a "substrate" is any material that has a surface to which functionalized gelatin layers and/or nanostructures (e.g., nanoparticles) can be applied as described herein. For example, a substrate can be a material with a relatively flat or curved surface such as a plastic or glass microscope slide. In other implementations, the substrate can be a device with a complex, three-dimensional surface, such as the one or more channels in a microfluidic device, or the substrate can be a bead or particle or a collection of a plurality of beads or other particles of various sizes, e.g., microbeads or micro-particles, and materials, e.g., glass, ceramic, metal, or plastic, to the surface of which the functionalized gelatin can be applied.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF FIGURE DESCRIPTIONS

FIGS. 12A-D are graphs depicting a comparison of EGFvIII mRNA quantification in serum and plasma-derived EVs using droplet digital PCR on patient samples.

Figure 13A:
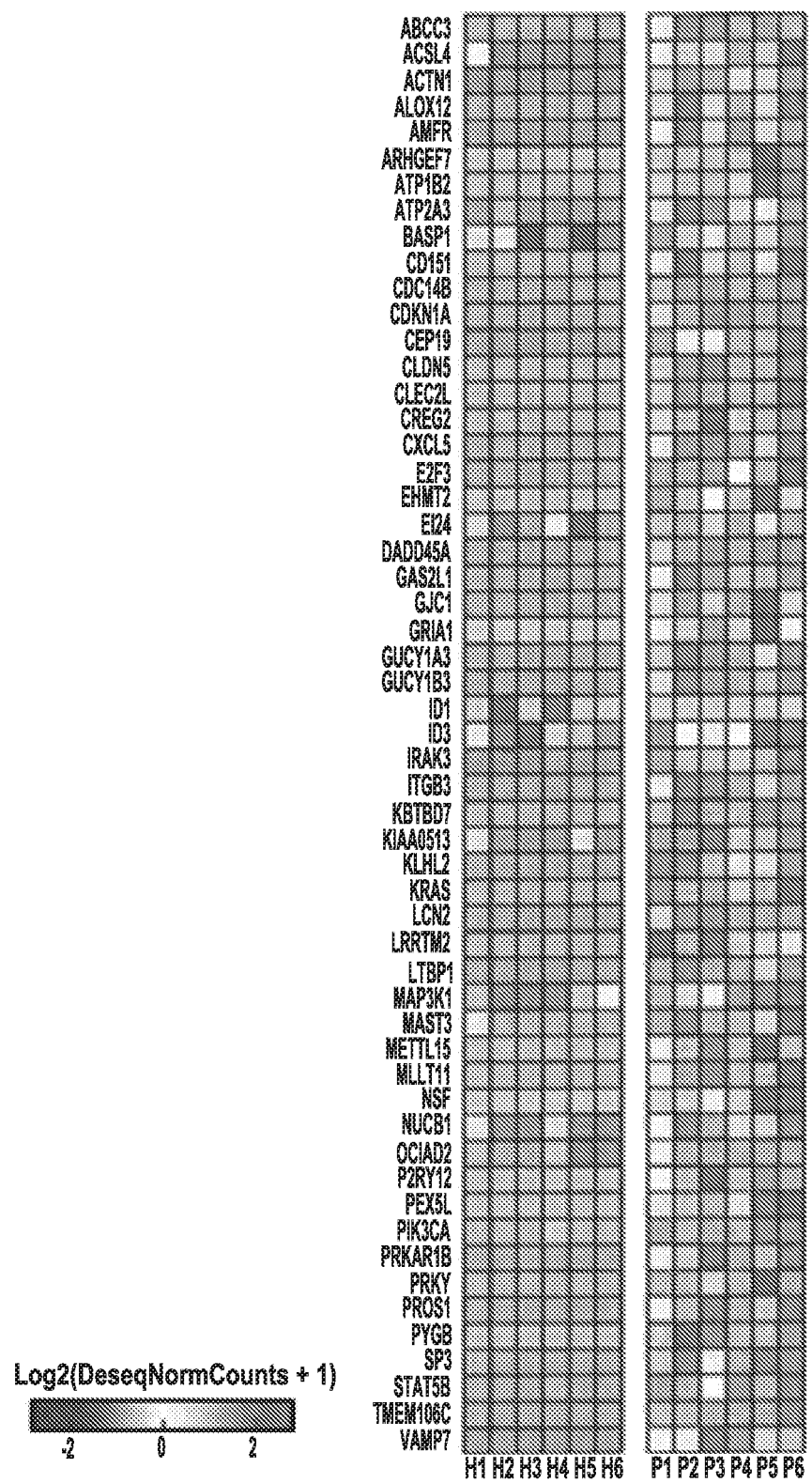
Figure 13B:
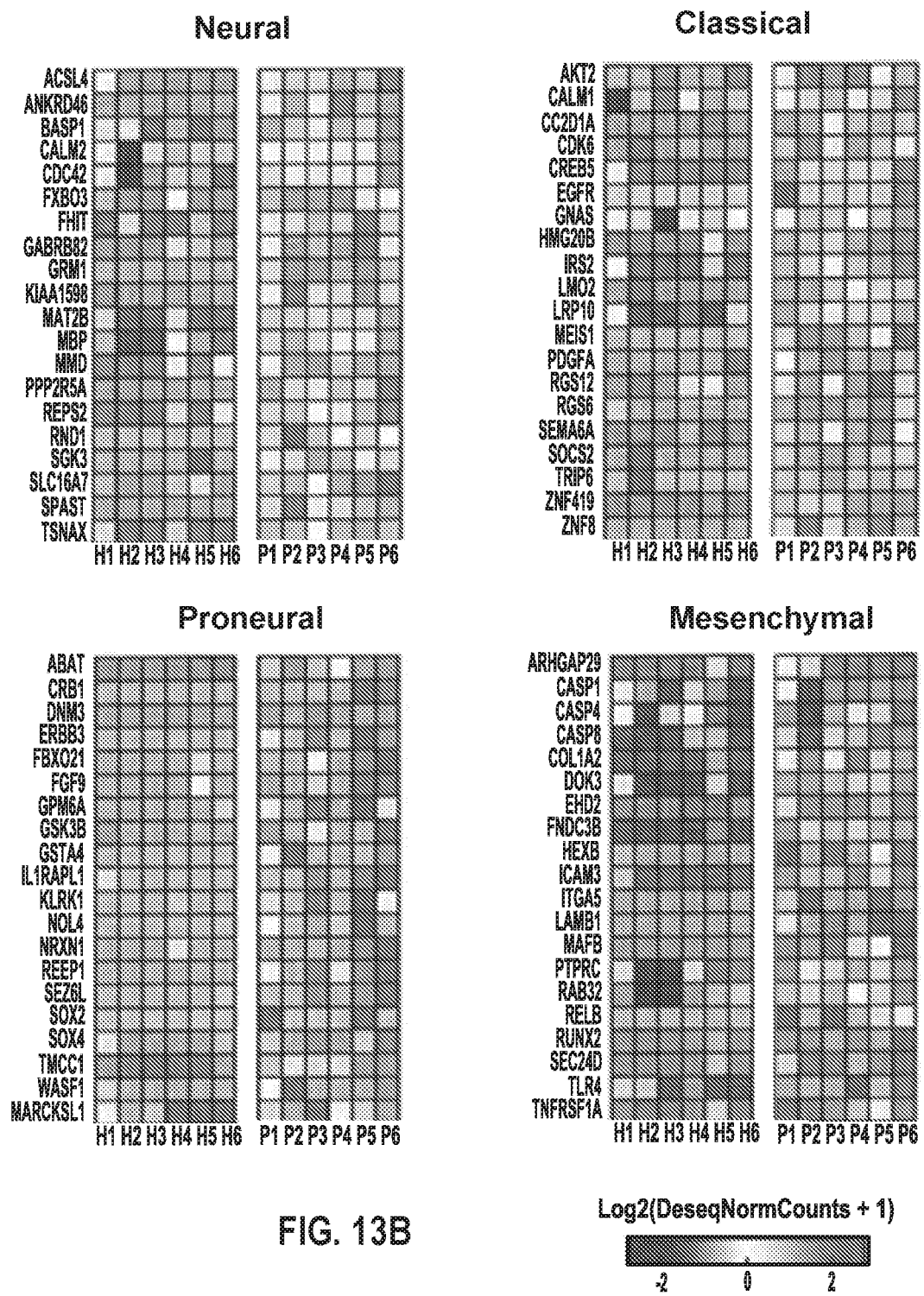

FIG. 13 is an RNA expression heatmap representation of RNA from EVs isolated using microfluidic devices described herein.

DETAILED DESCRIPTION

The present disclosure features microfluidic systems that can be used to isolate and capture target EVs from a fluid sample (e.g., bodily fluids such as human serum or plasma) for clinical investigation. The systems include a microfluidic device with channels coated functionalized with antibodies specific to target EVs. The channels include herringbone grooves to induce chaotic mixing to maximize interactions between target EVs in the fluid sample and antibodies immobilized on the surface of the channels. The surface of the channels can also be coated with a thermally responsive nanostructured substrate to allow extraction of capture target EVs for downstream characterization and clinical investigation.

As discussed below, the microfluidic systems can efficiently capture target EVs from fluid samples. Surfaces of the channels within the microfluidic device can be functionalized with antibody cocktails that allow for specific and rapid isolation of the target EVs. The captured target EVs can subsequently be released to allow analysis of biological cargo. In some instances, the surface of the channel can include nanostructured interfaces and linker molecules of a specified length or weight (e.g., 2.4 kDa) to improve specificity in capturing target EVs.

As discussed below, the clinical potential of the microfluidic systems was evaluated by identifying EGFRvIII mutations in serum/plasma from GBM patients. RNA sequencing analysis on the captured EVs revealed the presence of more than 50 genes specific to GBMs, as well as a variety of the GBM subtype-identifying mRNAs (neural, pro-neural, mesenchymal, and classical).

Once target EVs have been captured using the microfluidic device, the captured EVs can then be characterized and/or processed for further clinical investigation. For example, mRNA contained in target EVs captured on the surface of the microfluidic device can be isolated and analyzed as a diagnostic tool for a disease condition associated with the target EVs. As another example, quantitative PCR can be used to quantify the presence of target EVs in a liquid sample.

The descriptions below initially discuss concepts relating to target EVs and their isolation and capture from fluid samples. Systems and methods that can be used to isolate and capture target EVs from a fluid sample are then discussed. The description then focuses on methods of isolating and analyzing RNA from specific EVs that have been captured using the microfluidic system discussed throughout this disclosure. Downstream processing techniques for analyzing captured specific EVs are then discussed. Experimental results of exemplary implementations of the microfluidic system then further described.

I. Overview of Extracellular Vesicles

EVs are a heterogeneous group of cell-derived membranous structures that includes exosomes and microvesicles originating from the endosomal system or are shed from the plasma membrane. EVs can be present in biological fluids and are involved in multiple physiological and pathological processes. For example, EVs can be considered as an additional mechanism for intercellular communication, allowing cells to exchange proteins, lipids, and genetic material. Knowledge of the cellular processes that govern extracellular vesicle biology can be essential to shed light on the physiological and pathological functions of these vesicles as well as on clinical applications involving their use and/or analysis.

Different specific types of EVs can be used as biomarkers of various pathological conditions. For example, identification of EVs produced by tumor cells (i.e., tumor-derived EVs) in a biological sample can be used to diagnose a patient with cancer. Because a biological sample can include different types of EVs, clinical diagnostic techniques based on EV identification and characterization often require the ability to selectively capture and isolate target EVs (e.g., EVs produced by tumor cells) while avoiding capture of non-target EVs (e.g., EVs produced by platelets, EVs produced by normal healthy cells). The specificity of a target EV isolation technique thereby indicates its potential likelihood of being successfully applied as a diagnostic tool.

Different types of target EVs can captured and isolated depending on the clinical application. For instance, isolation and capture of tumor-derived EVs can be used to identify the presence of tumor cells producing the tumor-derived EVs in a biological sample. As an example, target EVs can represent EVs produced by GBM cells in a sample from a patient with glioblastoma. In other examples, target EVs can represent EVs produced by other types of tumor cells that are associated with different pathological conditions, such as pancreatic, prostate, lung, breast, bladder, liver, and head and neck cancers. Target EVs can also be derived from cells associated with the tumor or tumor microenvironment, such as macrophages, neutrophils, immune cells, and T-cells. Isolation of these cell-specific EVs can help in the identification of patients that will respond to specific treatments, with a direct interest in immunotherapy. Further, these EVs can help to identify patients that are responding to the treatment already administered. Other non-cancer disease states (or injuries) would include cardiac events, stroke, neurological conditions (Parkinson's, Huntington's, Alzheimer's, Schizophrenia, Traumatic Brain Injury) as well as monitoring mental health and treatment response.

In other instances, target EVs can represent EVs produced by other types of cells of interest. For example, EVs released from putative donor organs can be used to monitor the 'fitness' of the organs for transplant. All biological cells release EVs, and as such, they can represent a biomarker for overall organ health and state. Examples include cardiac, kidney and liver EVs. Immune response and allergic reactions could also be monitored through EV release from specific cells, while their production in animal products (e.g., cow's milk) help to identify both fertility states as well as a means for quality control of the food source.

II. Systems for Isolating and Capturing Overview

The systems and methods disclosed herein improve the specificity of target EV capture and isolation from a biological fluid and thereby address various challenges associated with distinguishing between target EVs (e.g., EVs produced by tumor cells) and non-target EVs (e.g., EVs produced by normal cells).

While this disclosure references tumor-derived EVs as target EVs (e.g., EVs produced by GBM cells), these descriptions are intended to be exemplary and should not be understood to limit the scope of the systems and methods disclosed herein. Other types of target EVs are contemplated to be capable of being isolated and captured by the systems and methods disclosed herein. For example, in some implementations, target EVs can include various types of tumor-derived EVs, such as pancreatic tumors. In other implementations, target EVs can include EVs produced cells other than tumor cells that are useful for clinical investigation, such as predicting patients that would receive the greatest benefit from immunotherapy. Alternatively, Isolated EVs from immune cells (or tumor cells) may also help in the pre-conditioning or even design of CAR-T-Cells.

Figure 1A:
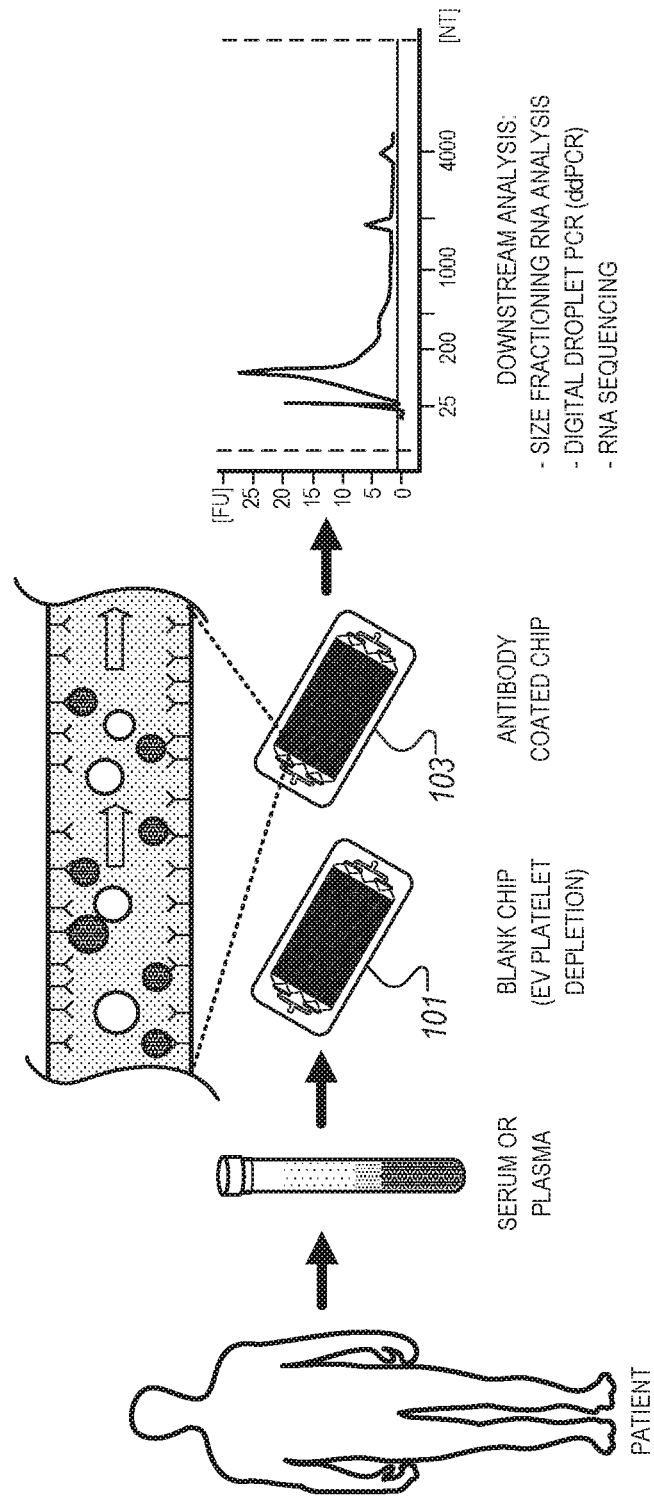
FIG. 1A is a schematic representation of patient sample processing using a microfluidic device.
Figure 1B:
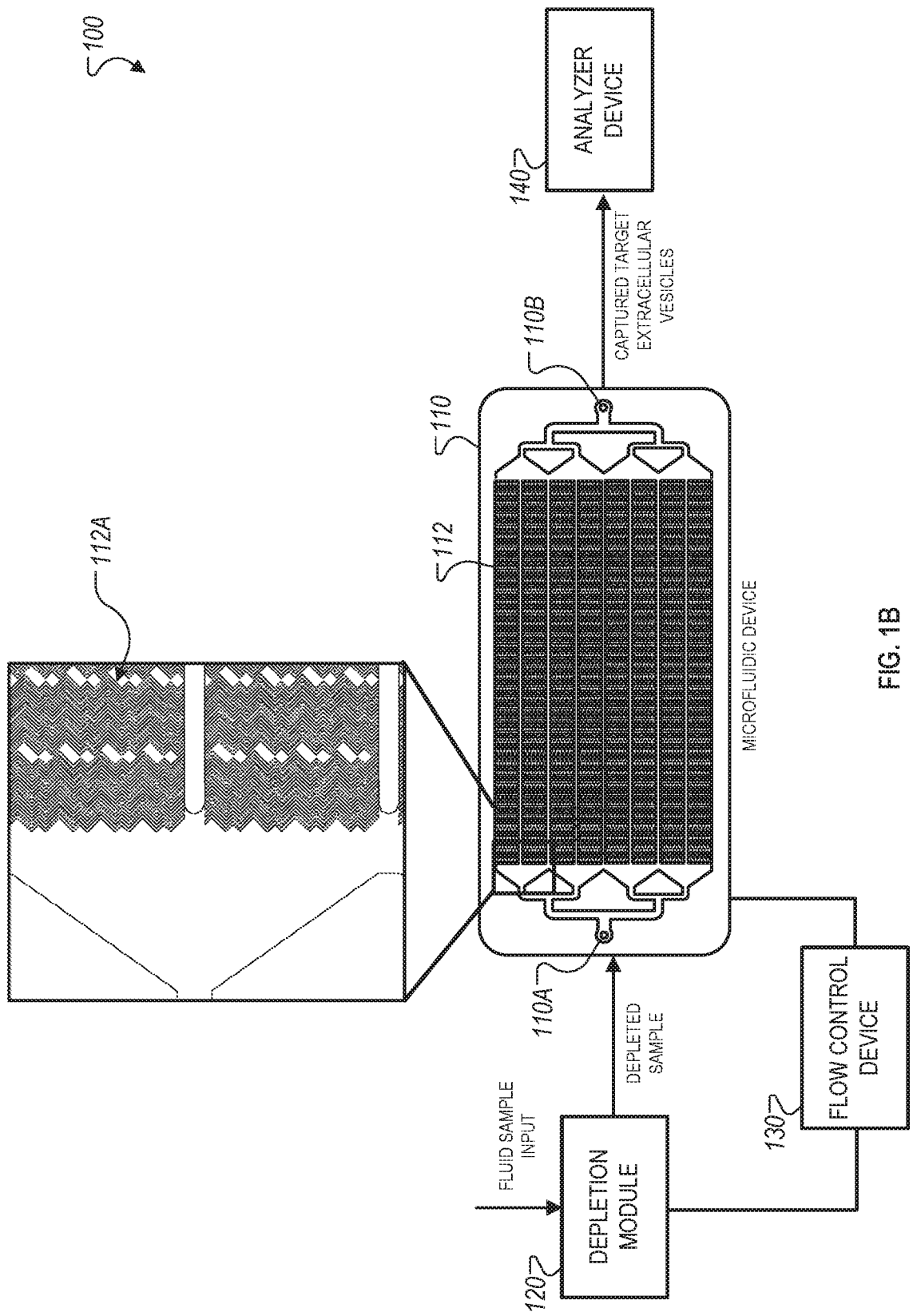
FIG. 1B is a schematic representation of a microfluidic system that can be used to isolate EVs.
Figure 1C:
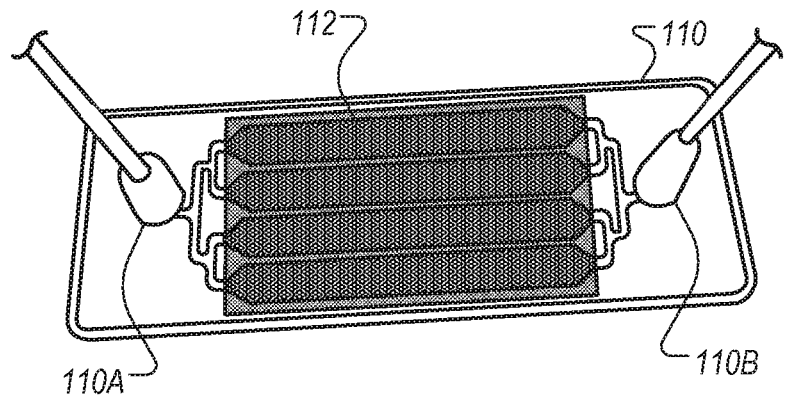
FIG. 1C is a schematic representation of a microfluidic device.
Figure 1D:
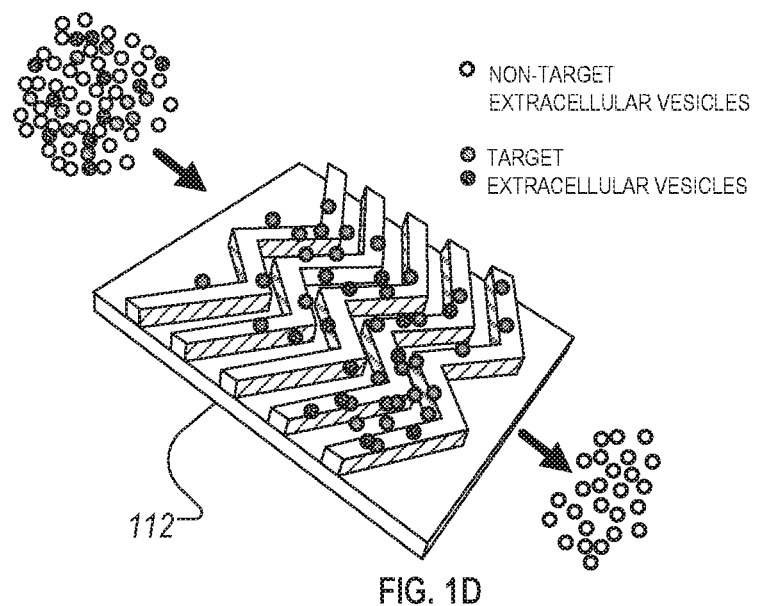
FIG. 1D is a schematic representation of herringbone pattern grooves in a portion of a channel of the microfluidic device depicted in FIG. 1C.

FIG. 1A is a schematic representation of an example of patient sample processing using a microfluidic system that includes microfluidic devices depicted in FIGS. 1B-D. In this example, a fluid sample (e.g., serum or plasma) is collected from a patient and processed in series using two microfluidic devices. The fluid sample is initially flowed through a depletion module 101, which can be a first microfluidic device, for depletion of non-target EVs (e.g., EVs produced by platelets and/or other healthy cells). A portion of the fluid sample that exits the microfluidic device 101 is then introduced into a capture module 103, which can be a second microfluidic device configured to capture target EVs from the fluid sample. The target EVs that have been captured on the microfluidic device 103 can then be investigated using different types of downstream analysis techniques discussed in greater detail below. For example, the captured target EVs can be investigated using size fractioning RNA analysis, digital droplet PCR (ddPCR), and RNA sequencing.

The depletion and capture modules, e.g., microfluidic devices, 101 and 103 can include channels with herringbone grooves that are used to induce chaotic mixing of the fluid introduced into the channels. The herringbone grooves are discussed in greater detail with respect to FIGS. 1B-D. The microfluidic device 101 is a blank microchip that has surfaces that are not coated with antibodies. The microfluidic device 103 includes one or more surfaces that are coated with antibodies using surface chemistry that is discussed in more detail with respect to Examples 4 and 5 below. The microfluidic device 103 allows specific capture of target EVs based on, for example, interactions between antibodies immobilized on a surface of a microchannel and antigens present on surfaces of the target EVs.

FIG. 1B is a schematic representation of a microfluidic system 100 that can be used to isolate target EVs. The system includes a microfluidic device 110, a depletion module 120, a capture module 110, a flow control device 130, and an analyzer device 140.

In general, the system 100 can be used to isolate and capture target EVs from a fluid sample using the capture module 110, such as a microfluidic device. The target EVs captured on the microfluidic device 110 can then be characterized, investigated, or otherwise processed downstream by the analyzer device 140. For example, RNA can be extracted from captured target EVs and evaluated by the analyzer device 140 for the presence of specific genes that are associated with a pathological condition. In some implementations, target EVs captured on the microfluidic device 110 can be extracted to another medium prior to analysis by the analyzer device 140. For example, the captured target EVs can be extracted from the channels of the microfluidic device 110 and further processing and investigation.

The microfluidic device 110 can be a cartridge that permits the flowing and processing of a liquid sample and an antibody reagent through a fluidic circuit to perform EV capture and isolation as described herein. The fluidic circuit of the microfluidic device 110 can include one or more inlets 110A through which sample fluids are introduced into the microfluidic cartridge, one or more microfluidic channels (or chambers) 112 through which the sample fluids flow, and one or more outlets 110B through which the sample fluids exit the microfluidic channels or chambers.

As shown in FIG. 1B, the channels 112 have columns of herringbone patterns 112A, e.g., as described in US Patent Application No. US2015/0377753, which is incorporated herein by reference in its entirety. Each column of herringbone patterns is positioned next to an adjacent column of patterns such that, an apex of a "V" shaped groove in the column is aligned with an apex of the "V" shaped groove in the adjacent column. The apexes of both grooves can lie on a line perpendicular to a principal axis passing through a channel of the microfluidic device 110. If all grooves in a column are equidistantly formed in the channel of the microfluidic device 110, then all grooves in the device will be aligned with each other. In some implementations, a column of herringbone patterns can be offset from an adjacent column. For example, the apex of a "V"-shaped groove in the column can be offset by 10 µm from the apex of a "V"-shaped groove in the adjacent column. The offset column design can further promote mixing. In some implementations, the multiple columns in the microfluidic device 110 can include symmetric grooves and asymmetric grooves randomly interspersed in each column. The forming of interspersed grooves promotes transverse movement of the fluid and the particles suspended in them, thereby increasing the number of cell-channel wall interactions and consequently increasing cell capture.

The depletion module 120 can be a device that is used to remove non-specific EVs, e.g., EVs produced by platelets and EVs produced by healthy cells, from a sample fluid. As discussed above with respect to FIG. 1A, a liquid sample is initially introduced into the depletion module 120 prior to prior to introduction into the microfluidic device 110 to improve the specificity of binding target EVs in the microfluidic device 110. In some implementations, the depletion module 120 is a blank microchip that has the same structures and features as the microfluidic device 110, but does not have functionalized channel surfaces that are coated with binding moieties that specifically bind to target EVs. In such implementations, the depletion module 120 can include channels with herringbone pattern grooves 112A to increase the surface area and induce chaotic mixing in the same manner as discussed above with respect to the microfluidic device 110. The depletion module works, because non-specific EVs, e.g., from platelets, naturally bind to surfaces of substrates, and thus are removed from the sample fluid as it flows through the depletion module, even without the use of any binding moieties. On the other hand, target EVs, such as from cancer cells, naturally resist binding to surfaces, and thus do not adhere to surfaces of solid substrates.

In some implementations, the depletion module 120 can include binding moieties that bind to non-specific EVs. For example, such binding moieties can bind to tetraspanins, e.g., CD63 or CD8, that are associated with membranes of many types of intracellular vesicles, to remove non-target EVs from a fluid sample.

In some implementations, the depletion device 120 can be a device that provides a high surface area, such as a sponge, a mesh, a forest of fibers, or packed colloids, for removal of non-target EVs from a liquid sample prior to introduction into a microfluidic device that is coated with binding moieties specific to the target EVs. The depletion device 120, in such implementations, can enable a flow rate that induces microvorticies to enable depletion in the same manner as discussed above.

The flow control device 130 can be any type of fluid delivery device used to introduce a sample fluid into a fluidic circuit. For instance, the flow control device 130 can be a peristaltic pump, a syringe pump, a pressure controller with a flow meter, or a pressure controller with a matrix valve. The flow control device 130 can be attached to tubing that attaches to the inlet port of the microfluidic device 110 to introduce the sample fluid into the channels of the microfluidic device 110. In some instances, the flow control device 130 is also capable of adjusting the flow rate of the sample fluids introduced into the microfluidic chamber according to a predetermined or user-adjusted program. This predetermined program is based on a specific sequence that involves flowing the liquid sample for a certain period of time at certain speeds. For example, the predetermined program can involve flow rates between around 0.5 mL/h to 20 mL/h, e.g., 0.7, 1.0, 2.0, 3.0, 4.0, 5.0, 6.0, 7.0, 8.0, 9.0, 10, 12.5, 15, 17.5, or 20.0 ml/hr. In some instances, the upper limit can be extended by increasing the surface area of channels in the microfluidic device.

The analyzer device 140 can be a computer-controlled device that is capable of acquiring, processing, and/or storing data associated with target EVs captured on the microfluidic device 110. For example, in some implementations, the analyzer device 140 is an RNA sequencing device, e.g., 10×, IlluminaMiSeq, BioRAD ddPCR, which is capable of sequencing cytoplasmic or nuclear RNA from captured target EVs. In such implementations, the analyzer device 140 can be used for size-fractioning RNA. In other implementations, the analyzer device 140 can be a microscopic device (e.g., a confocal microscope, fluorescent microscope) that is used to investigate target EVs that have been captured in the channels of the microfluidic device 110. In some other implementations, the analyzer device 140 can be a polymerase chain reaction (PCR) system that is capable of nucleic acid application and detection.

A. Microfluidic Device

FIG. 1C is a schematic representation of the microfluidic device 110 depicted in FIG. 1B. FIG. 1D is a close-up schematic representation of herringbone pattern grooves and/or ridges in a portion of a channel of the microfluidic device 110. As shown in FIG. 1D, the herringbone pattern grooves and/or ridges can be used to capture target EVs from a fluid sample that flows through a channel of the microfluidic device 110. The fluid sample can include both target EVs (e.g., tumor-derived EVs) and non-target EVs (e.g., EVs produced by platelets). The surfaces of the channel can be coated with antibodies that allow for the selective capture of target EVs but not non-target EVs. Thus, as a fluid sample flows through the channel, target EVs interact with binding moieties, e.g., antibodies or aptamers, immobilized on surfaces of the herringbone groove patterns as non-target EVs flow through the channel with the flow of the liquid sample.

The herringbone groove patterns can be arranged in a column such that the grooves in the path of the fluid disrupt fluid flow. In some implementations, depending upon flow velocity and the dimensions of the grooves, specifically, for example, a size of the grooves and an angle between the two arms of a groove, the disruption in the fluid flow leads to a generation of microvortices in the fluid. For example, the microvortices are generated because the grooves induce fluid flow in a direction that is transverse to a principal direction of fluid flow, i.e., the axial direction. The microvortices can be induced in flow rates ranging from about 0.5 mL/h to 100 mL/h, e.g., 1, 5, 10, 25, 50, 75, 100 mL/h.

In some implementations, although microvortices are not generated, the grooves induce sufficient disruption to alter the flow path of portions of the fluid to increase wall-particle interactions.

The heights of herringbone pattern grooves can be varied in different implementations. In general, the choice of groove heights can depend on factors including channel dimensions, particle properties including size, density, and the like, and particle suspension flow rates. Although deeper grooves offer more disruption, other factors can impose limits on groove heights. For example, up to a certain limit, the groove height can be increased in proportion with the channel height. The channel height, and consequently the groove height, can depend upon the particle to channel surface contact area. An increase in channel dimensions can cause a decrease in particle-channel interactions as surface contact area available for the particles to interact decreases relative to the cross-sectional flow area. A lower limit on the channel height, and consequently the groove height, can be imposed to prevent clogging.

In some implementations, a ratio between groove height and channel height can be less than one, for example, in a range between 0.1 to 0.6. In some implementations, the ratio can be equal to one (e.g., the groove height can be equal to the channel height), or can be greater than one (e.g., the groove height, for example, 60 μm, can be greater than the channel height, for example, 50 μm).

The shape of the grooves, from a top view, can also be different from a "V" shape, for example, "U" shape, "L" shape, and the like. In some particular implementations, the groove and channel heights can between approximately 25 μm to 200 μm, e.g., 25, 50, 100, 125, 150, 175, 200 μm. In some implementations, the grooves are not perfectly square-shaped from a top view, i.e., with apexes formed by a ninety-degree angle, and instead have different angles, e.g. 60, 65, 70, 75, 80, 85, 95, 100, 105, 110 or other degrees. In other embodiments, the apexes can be rounded rather than having a sharp angle.

A channel formed in a microfluidic device can be treated to capture target EVs suspended in a fluid flowing through the channel. A particle capture efficiency of the microfluidic device can be defined as a ratio of a number of particles captured in the channel and a total number of particles flowed through the channel. As described above, grooves (or ridges) are formed extending into (or out of) the walls of the channel to create flow patterns in the fluid that promote an interaction between the particles suspended in the fluid and inner surfaces of the walls of the channel. The increased interaction can lead to an increase in a number of particles captured in the channel, and consequently, in the particle capture efficiency of the microfluidic device. The efficiency can further be increased by tailoring structural features of the microfluidic device including, for example, device substrate material, channel and groove dimensions, and the like, as well as fluid flow parameters such as flow rates based on types of particles and the types of fluids in which the particles are suspended. An example of such a microfluidic device manufactured using soft lithography techniques is described with respect to FIGS. 1B and 1C. As described below, particles are captured in the channel of the microfluidic device 110 by forming grooves in a wall of the channel, coating binding moieties on the inner surfaces of the walls of the channel, and flowing a sample fluid that may contain EVs suspended in the fluid through the channel.

In some implementations, the channel can have a rectangular cross-section including two side walls, and an upper wall formed in the upper substrate. Terms of relative location such as, for example, "upper" and "lower" are used for ease of description and denote location in the figures rather than necessary relative positions of the features. For example, the microfluidic device 110 can be oriented such that the grooves are on a bottom surface of the channel or such that a central axis of the channel extends vertically. Alternatively, the cross-section of the channel can be one of several shapes including but not limited to triangle, trapezoid, half-moon, and the like. The lower substrate can form the lower wall of the channel once bonded to the upper substrate. In some implementations, the channel includes multiple grooves formed in the upper wall of the channel. Alternatively, the grooves can be formed in any of the walls, and/or can be formed in more than one wall of the channel. The grooves can span an entire length of a wall, or only a portion of the wall.

B. Surface Chemistry

Surfaces of the channel formed in the microfluidic device 110 can be functionalized to enable selective capture and isolation of target EVs from a fluid sample (e.g., serum or plasma). Various surface chemistries can be applied to the surfaces to enable, for example, the type of target entity to be captured in the channel of the microfluidic device.

Figure 2A:
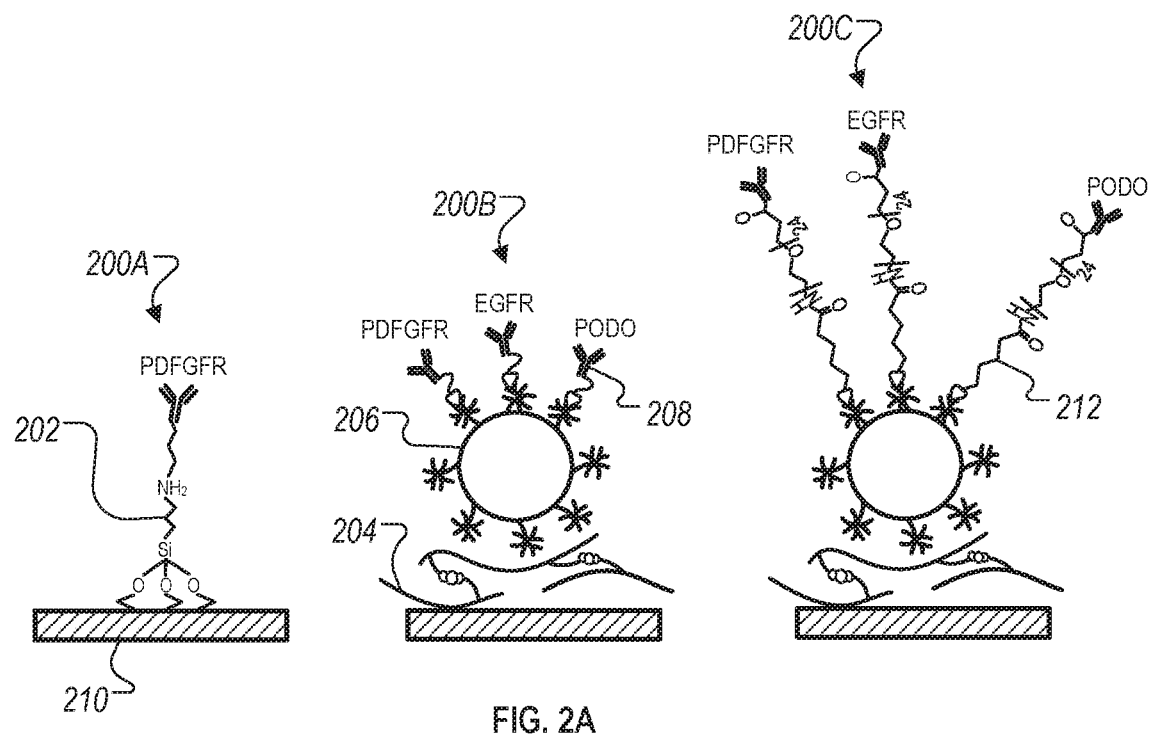
FIG. 2A is a graph of different surface chemistries for immobilizing antibodies onto a surface of the microfluidic device depicted in FIG. 1C.

FIG. 2A is a schematic representation of different surface chemistries for immobilizing binding moieties, e.g., antibodies, aptamers or ligands from a ligand binding pair, heparin, lectins, glycoproteins, onto a surface of a channel of the microfluidic device 110. The surface chemistry is applied to a surface of a substrate 210 that forms a wall of a channel of the microfluidic device 110. Generally, different surface chemistries can be applied to specify the target EVs to be captured using the microfluidic device 110, for example, by varying the antibodies that are immobilized on the surface of the substrate 210. In other examples, such as those shown in FIG. 2A, different antibody immobilization strategies can be used based on differences in biophysics of capture for different types of target EVs. For example, 100 nm diameter EVs within the microfluidic device 110 exhibit different biophysics compared to 10-20 μm whole cells.

Surface chemistry 200A represents an immobilization strategy in which a zero-length spacer 202 is immobilized directly on the surface of the substrate 210. In this example, the spacer 202 is bound to a platelet-derived fibroblast growth factor receptor (PDFGFR) antibody at a first end and is bound to the surface of the substrate 210 at a second end. Surface chemistry 200B in FIG. 2A represents an immobilization strategy in which layers of gelatin 204 are functionalized onto the surface of the substrate 210. In this example, the top layer of the layers of gelatin 204 is optionally bound to nanostructures, e.g., nanoparticles, 206 that immobilize zero-length linker molecules bound to binding moieties 208, such as antibodies to PDFGFR, endothelial growth factor receptor (EGFR), and podoplanin (PODO).

Surface chemistry 200C shown in FIG. 2A represents an immobilization strategy in which fixed-length linker molecules 212 are bound to nanostructures 206 to provide an even greater surface area. Surface chemistries 200A and 200B were previously applied for immunoaffinity capture of μm-size particles (e.g., circulating single or clusters of tumor cells), and work to capture EVs, but surface chemistry 200C was even more effective to capture EVs.

The flexible linker molecules 212 can have a molecular weight between approximately 1.0 to 5.0 kDA, e.g., 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.75, 4.0, 4.25, 4.5, 4.75, or 5.0 kDa. The flexible linker molecules 212 can be made of PEG, dextran, or any other suitable polymer that is capable of binding to the nanostructures 206 and binding moieties 208.

In some implementations, the flexible linker molecules 212 be linker molecules with different geometries, such as branched linkers, where the first end of the linker molecules 212 is attached to the gelatin 204 or the nanostructures 206, and the other end has two or more branches, with a binding moiety attached to each branch of the linker.

The layers of gelatin 204 coated on the surface of the substrate 210 include multiple layers, as described, for example, in US Patent Application No. US2015/0369804. For example, the surface of the substrate 210 can be coated with a first layer of gelatin that is functionalized with a first member of a binding pair, e.g., biotin. The first layer of gelatin is bound to nanostructures 206 by physical adsorption. A second layer of gelatin also functionalized with a plurality of the first members of the binding pair is bound to the first layer via a plurality of second members of the binding pair, e.g., avidin or streptavidin to bind to biotin, that are associated with the first members of the binding pair on both the first and the second layers. Optionally one or more subsequent layers of functionalized gelatin can be included such that each new layer is bound to a previous layer by second members of the binding pair.

When added to the capture module, either bound directly to the channel walls or bound to a top layer of a gelatin coating, the nanostructures 206 can be nanoparticles, nanospheres, nanotubes, or nanorods. In some implementations, the nanostructures 206 are bound to a member of a binding pair and to one or more binding moieties (e.g., antibodies) that selectively bind to the target EVs. The nanostructures can be bound to the substrate directly or to the top layer of gelatin by a second member of the binding pair. The nanostructures add surface area, e.g., surface roughness, to the substrate or the top gelatin layer and can create two additional benefits: (i) higher local concentration of the binding moieties per unit area, and (ii) multiple orientations of the binding moieties around the surface of the nanostructures that can provide high EV capture efficiency.

Figure 2B:
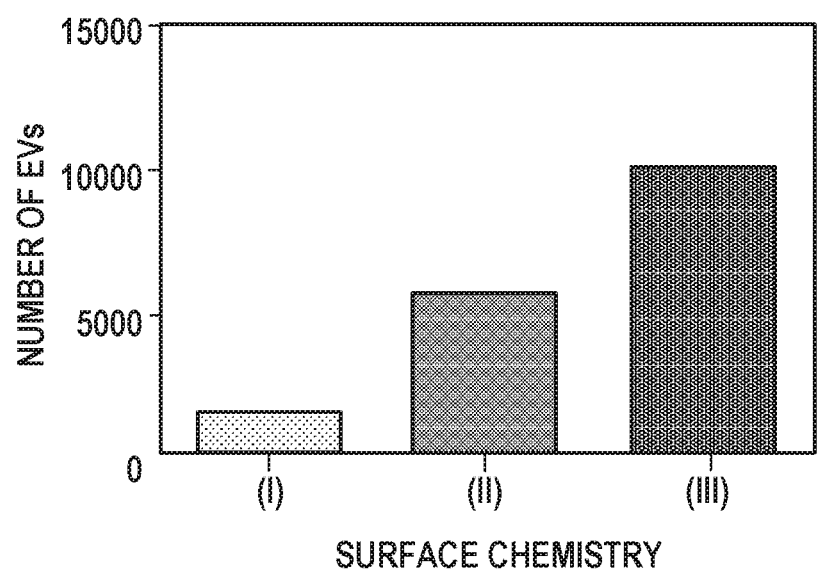
FIG. 2B is a graph depicting a comparison of EV capture on the surface of a microfluidic device using different surface chemistries.

FIG. 2B is a bar graph depicting a comparison of EV capture on the surface of a channel within the microfluidic device 110 using surface chemistries 200A (I), 200B (II), and 200C (III). An experiment was conducted to investigate the number of EVs that were captured using the different surface chemistries. Application of the surface chemistry 200C resulted in an approximately two-fold increase in EV capture on the microfluidic device 110 compared to surface chemistry II (200B). Moreover, as described in Example 3 below and depicted in FIG. 6, the effect of molecular weight of the linker molecules 208 on EV capture was also investigated to identify the most effective molecular weight of the linker molecules 208 (e.g., approximately between 1.8-4.8 kDa). Once target EVs have been captured on the surface of the substrate 210, the captured target EVs can then be released from the substrate 210 via either of release mechanisms discussed in detail below.

III. Methods for Isolating and Capturing Target EVs

A. Device Fabrication

The microfluidic device 110 can include an upper substrate bonded to a lower substrate that can be fabricated using an appropriate material. For example, the upper substrate can be fabricated using an elastomer such as, for example, polydimethylsiloxane (PDMS), and the lower substrate can be fabricated using glass, PDMS, or another elastomer. Alternatively, or in addition, the substrates can be manufactured using plastics such as, for example, polymethylmethacrylate (PMMA), polycarbonate, cyclic olefin copolymer (COC), and the like. In general, the materials selected to fabricate the upper and lower substrates can be easy to manufacture, for example, easy to etch, and can offer optical properties that facilitate ease of testing. For example, the upper and lower substrates can be optically clear, and can be non-toxic so as to not negatively affect the cells or molecules attached to the substrate. In addition, the materials are preferred to exhibit no or limited auto-fluorescence. Further, the materials can be easy to functionalize so that analytes can be attached to the substrate. Furthermore, the materials can be mechanically strong to provide strength to the microfluidic device 110. The upper substrate can be securely fastened to the lower substrate, with a microchannel formed between them, as described throughout.

In one particular implementation, the microfluidic device 110 is a microchip that includes eight channels with herringbone pattern grooves as discussed above. The microchip is fabricated using standard photolithography techniques to produce, for example, a polydimethylsiloxane (PDMS) and glass device. Various stiffness can be used for the PDMS with a similar effect gained. 3D printing techniques may also be used to produce the microfluidic device 110. The microfluidic device fabrication is scaled up by plastic microinjection molding of cyclic olefin copolymer (COC) at thinXXS® Microtechnologies (Germany). In some implementations, other plastics, such as PMMA, may also be used to produce the microfluidic device 110. In such implementations, the microfluidic device 110 is manufactured in two separate molds—one for three-dimensional features, and another for a top layer that is subsequently put together by thermoplastic bonding. While the microfluidic device 110 is designed to allow for on-chip imaging and visualization of the captured particles, the flow pattern can continue through stacked layers of the channels, increasing throughput and surface area. The captured EVs could then be released for downstream visualization.

B. Gelatin Functionalization

The microfluidic device 110 can be formed by using a modified layer-by-layer (LBL) process. Such LBL process can start with obtaining a substrate, e.g., glass or PDMS. The substrate can be a microscope slide or one or more channels, e.g., within the microfluidic device 110. The substrate can then be exposed to a gelatin solution comprising gelatin functionalized with a plurality of the first members of a binding pair, e.g., biotinylated gelatin, at a concentration and for a period of time sufficient for the gelatin to bind to the substrate, e.g., 5, 10, 15, or 20 minutes, thereby forming a first layer of gelatin on the substrate by physical adsorption. The time of exposure is one factor in selecting the thickness of the coating, with the maximum thickness being attained at about 15 minutes. Longer times will not add much to the thickness and shorter times will result in a thinner coating. The exposure can be accomplished by flowing the gelatin solution over or onto the substrate and is done at room temperature. The idea is for the gelatin to adsorb to the substrate physically without gelling.

The layers of gelatin 204 can be formed by exposing a substrate to a gelatin solution that includes gelatin functionalized with a plurality of the first members of a binding pair, e.g., biotinylated gelatin, at a concentration and for a period of time sufficient for the gelatin to bind to the substrate, e.g., 5, 10, 15, or 20 minutes, thereby forming a first layer of gelatin on the substrate by physical adsorption. The time of exposure is one factor in selecting the thickness of the coating, with the maximum thickness being attained at about 15 minutes. Longer times will not add much to the thickness and shorter times will result in a thinner coating. The exposure can be accomplished by flowing the gelatin solution over or onto the substrate and is done at room temperature. The idea is for the gelatin to physically adsorb to the substrate without gelling.

The excess gelatin solution can be washed out with a buffer, e.g., phosphate-buffer saline (PBS). This physisorbed gelatin layer interacts strongly with the substrate, e.g., PDMS or glass surface, and is not sensitive to temperature changes up to 37° C. The thickness of the physisorbed layer also depends on the initial concentration of the functionalized gelatin solution, which can be about 0.1% to about 2.5%, e.g., about 0.5% to about 2%, about 0.5% to about 1.5%, about 0.6% to about 1.4%, about 0.7% to about 1.3%, about 0.8% to about 1.2%, about 0.9% to about 1.1%. All concentrations are weight/volume.

Next, the first layer of gelatin can be contacted with a solution that includes the second members of the binding pair, e.g., avidin, neutravidin, or streptavidin, for a period of time sufficient to enable the members of the binding pair to bind each other, e.g., 15 minutes. A second layer of gelatin can be formed by exposing the deposited layers to the functionalized gelatin solution again for a period of time sufficient to enable the first members of the binding pair on the gelatin in solution to bind the second members of the binding pair on the deposited layers, e.g., 15 minutes.

Thus, the second layer is bound to the first layer via a plurality of the second members of the binding pair that are associated with the first members of the binding pair on both the first and the second layers. The deposited second layer of gelatin can then be contacted with a solution that includes the second members of the binding pair again to allow the members of the binding pair to bind to each other. These steps can be repeated to form one or more subsequent layers of gelatin, each bound to a previous layer by the second members of the binding pair. The second and subsequent gelatin layers are temperature-responsive layers. The gelatin layers are formed at a temperature of about 10° C. to about 23° C.

Finally, the solidified gelatin layers can be contacted with a solution including the nanostructures 206 that are bound to the second members of the binding pair and to one or more binding moieties 208 that can selectively bind target EVs for a period of time sufficient for the nanostructures 206 to bind to the functional groups on the layers of gelatin 204, e.g., 30 minutes. The nanostructures 206 can be about 50 to 250 nm, e.g., 75 to 150 nm, e.g., 100 nm, in size and can be, for example, nanoparticles, nanotubes, nanorods, or nanospheres as discussed above.

C. Microfluidic Surface Modification

As discussed herein, different surface chemistries can be evaluated to identify an optimal configuration for functionalizing binding moieties onto one or more surfaces of a channel of the microfluidic device 110.

In one particular implementations, capture antibodies are immobilized onto a channel surface using a surface modification protocol discussed below. A silane-based chemistry based on a 4% (v/v) solution of 3 mercaptopropyl trimethoxysilane (Gelest®, Morrisville, Pa.) in ethanol is initially used for surface modification. The solution is incubated for one hour at room temperature. N-y-malemidedobutyryloxy succinimide ester (Pierce Biotechnology, Rockford, Ill.) at 0.01 μg mL is incubated in ethanol for 30 min at room temperature in a channel of the microfluidic device 110. After washing the microfluidic device 110 with phosphate buffered saline (PBS), neutravidin (Pierce Biotechnology) at 10 μg mL is incubated in the device at 4° C. and stored. Nanostructured substrates can then be tested for antibody functionalization as discussed below.

An LBL technique can be used to incorporate biotin-gelatin layers on the surface of the microfluidic device 110 as discussed above. Biotin-gelatin alone is used as the cationic and ionic polyelectrolyte due to its polyampholyte behavior near neutral pH. Additionally, neutravidin is used to crosslink the thin gel through biotin-streptavidin binding. Each layer of biotin-gelatin at 1% (w/v) is flushed directly in the plasma activated channels and incubated for fifteen minutes. Any excess of polymer is removed with PBS and a solution of 100 μg mL-1 neutravidin is added and incubated for additional 15 minutes. A configuration of four layers is optimal for uniform coverage. The thickness of the nanocoating is characterized using a Dektak 150 Surface Profiler (Veeco, Plainview, N.Y.) with a value of approximately 150 nm. One last layer of 10 nm streptavidin-coated nanoparticles (Sperotech, Lake Forest, Ill.) is then incorporated into the film to create the nanostructured substrate and increase the local surface area of the added antibodies.

D. Antibody Immobilization

In some implementations, binding moieties that are immobilized onto one or more surfaces of a channel of the microfluidic device are antibodies specific to target EVs. Different antibodies can be used for isolation of target EVs, e.g., tumor-derived EVs, as discussed throughout.

In one particular example, immobilized antibodies include epidermal growth factor receptor variant III (EGFRvIII), epidermal growth factor receptor (EGFR) (AF231), human platelet-derived growth factor receptor (hPDGFR) (MAB1260), Podoplanin (AF3670), ephrin receptor A2 (EphA2) (AF3035, R&D Sytems, Minneapolis, Minn.), and the Cetuximab (ImClone LLC, Branchburg, N.J.). Each antibody is biotinylated with diverse length linker molecules to achieve an optimal EV capture efficiency as discussed below.

A zero-length linker molecule sulfo-Biotin-NHS (Thermo Fisher Scientific) is initially used according to manufacturer protocol as discussed above in reference to surface chemistry 200B. Elongate flexible linker molecules, e.g., poly ethylene glycol (PEG) linker molecules, with different molecular weights (Mw) are then used for antibody conjugation. For example, PEG linker molecules with molecular weights of 3 Da, 6 Da, 1.2 kDa, 2.4 kDa, 5 kDa, 10 kDa, 20 kDa are used.

Briefly, a 1 to 2 mg mL antibody concentration is buffer exchanged using a commercially available kit (CromaLink, Solulink, Calif.). Then, 100 μL of the antibody solution is mixed with NHS-PEG-Biotin (Creative PEG Works, Chapel Hill, N.C.) dissolved in 100% DMF. The reaction is allowed to proceed for two hours at room temperature. Optimal antibody/PEG-Biotin ratios were then calculated. After incubation, biotinylated antibodies are cleaned using a 7K molecular weight cut-off (MWCO) Zeba Column (Solulink, San Diego, Calif.) and stored at −80° C. The biotinylation process are verified using a commercially available ultraviolet (UV) probe (Solulink) for the low Mw 3 Da spacer. A biotin binding assay (HABA) (Thermo Fisher Scientific) is used for all the other conditions. Biotinylated antibodies are incubated in the microfluidic device 110 for 1 hour at 10, 20 or 100 μg mL in PBS containing 1% bovine serum albumin (BSA, Sigma-Aldrich).

E. Cell Culture

As discussed below, in some implementations the microfluidic system 100 can be used to capture and isolate target EVs produced by glioma cells in patient samples from patients with GBM. In such implementations, GBM20/3 and Gli36 cell lines are used in conjunction with the microfluidic device 110. The GBM20/3 and Gli36 cell lines can be generated in a laboratory setting. Initially, GBM20/3 and Gli36 wt are stably infected EGFRvIII (Gli36-EGFRvIII) glioma cells and cultured in DMEM (Invitrogen, Thermo Fisher Scientific) with 10% fetal bovine serum (FBS, Sigma-Aldrich) and 1% penicillin and streptomycin (P/S, Cellgro, Manassas, Vir.). Cells lines used are passaged using 0.25% trypsin/EDTA (Invitrogen, Thermo Fisher Scientific). Tumor cells were negative for *Mycoplasma* as routinely tested by an enzymatic assay (Promega, Madison, Wis.).

F. EVs Production and Spike Preparation

Figure 3:
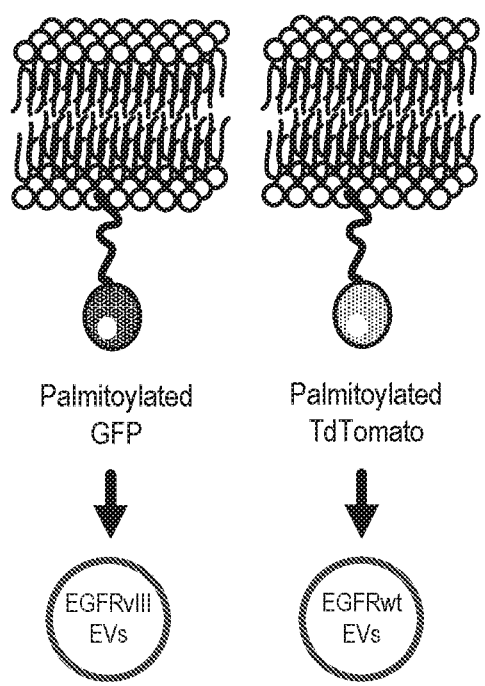
FIG. 3 is a schematic representation of fluorescently labeled EVs that can be used for detection of tumor-derived EVs from glioma cells.

FIG. 3 is a schematic representation of two fluorescently labeled EVs, EGFTvIII, and EGFRwt, that can be used for detection of target EVs from glioma cells. To generate the fluorescent EVs, Gli36 wt and Gli36-EGFRvIII glioma cells are stably infected with PalmtdTomato and PalmGFP, respectively, followed by fluorescent activated cell sorting using a BD FACSAria II Cell Sorter. The cells are then cultured in Dulbecco's Modified Eagle Medium (DMEM) containing 5% EV-depleted fetal bovine serum (FBS), which is prepared by ultracentrifugation at 100,000 g for 16 hours to deplete bovine serum EVs, for 48 hours. The conditioned medium is centrifuged for ten minutes at 300 g to eliminate cell debris, and the supernatants are centrifuged for 10 min at 2,000 g and filtered through a 0.8 µm filter. The EVs are pelleted by ultracentrifugation (Optima L-90K Ultracentrifuge, Beckman Coulter, Brea, Calif.) at 100,000 g for 70 minutes. Isolated EVs are resuspended in double 0.22 µm filtered PBS, quantified in size and number as discussed below. The isolated EVs are then spiked in serum or plasma from healthy individuals for testing the specificity of the microfluidic device 110. A 1:1 dilution of serum or plasma in PBS is prepared before running the device. A minimum of 2 mL of solution is used for every sample.

G. EV Quantification

Isolated EVs can be quantified using a tunable resistive pulse sensing (TRPS) qNano instrument (Izon Science, New Zealand). Different tunable pore size membranes (NP200, NP300, NP400, NP800) allowed the characterization of size multimodal EV distributions. Briefly, top and bottom fluid cell of the instrument are primed with PBS, and then appropriate calibration beads are forced to flow through the nanopore at pressures between 5 to 15 mbar by a water-based variable pressure module (Izon Science). A similar procedure is applied to EV samples. Acquired data is analyzed using a Control Suite Software provided by the same manufacturer.

For the characterization of captured EVs, two methods of release can be used. First, proteinase K is used to shave the EVs from the surface of the device and following recovery with applied flow. Second, a temperature gradient is applied to the surface of the microfluidic device 110 to disassemble the gelation nanocoating and release the EVs in solution.

H. Microfluidic Isolation of EVs

In some implementations, two or give microfluidic devices are run in series, depending on the type of samples. For spike EV or patient samples, two or are chips are used, respectively. In such implementations, the first microfluidic device is a blank microchip with no functionalization and used to deplete EVs from platelets, as discussed above with respect to the patient sample processing technique depicted in FIG. 1A. Serum or plasma is pneumatically driven through the microfluidic devices at a flow rate of 1 mL hr for two hours. The microfluidic device is washed with 2.5 mL of PBS at 2.5 mL/hr to remove any nonspecifically bounded EVs.

I. Isolation of EVs with Magnetic Beads

In some implementations, captured target EVs are conjugated with magnetic beads and are isolated by applying a magnetic force. For example, biotinylated Cetuximab with PEG linker molecules are immobilized with streptavidin-coated magnetic particles (3 µm, Sperotech, Lake Forest, Ill.) for 1 hour. The conjugated particles are incubated with spiked Gli36-EGFRvIII EVs in plasma for hours. Captured EVs are then pulled down by a magnetic force applied using a magnet, and gently re-suspended in 100 µL PBS for downstream analysis as discussed below.

IV. Downstream Processing Techniques for Analyzing Captured Target EVs

Target EVs that have been captured in channels of the microfluidic device 110 can be isolated for downstream processing and evaluation using various techniques, as discussed below.

Target EVs can be selectively captured from a liquid sample by contacting the liquid sample to the bioresponsive nanostructures disclosed herein to enable the one or more binding moieties to bind to target particles in the sample. The target EVs can then be released from a substrate, e.g., a slide or a channel within a microfluidic device, via either of two release mechanisms. First, by increasing temperature, e.g., over 30° C., e.g., 37° C., capture particles can be released in a bulk fashion. Second, by increasing a localized shear stress in the gelatin, e.g., by applying a frequency-controlled force with a vibrating device, e.g., using microtip devices, single cells can be selectively released from the substrate. The versatility of the capture and isolation techniques allows a practitioner to perform various assays with low or high complexity, as discussed below. For low complexity assays such as cell enumeration, culturing and staining, bulk release is sufficient. For high complexity assays such as single cell genomics, the selective release may be preferred.

Selective release occurs when a localized shear stress is generated in the gelatin layer, e.g., by applying a frequency-controlled force with a vibrating device, e.g., a microtip device, to the gelatin layers. The microtip device can produce a controlled vibration at the surface of the gelatin such that the gelatin is locally removed by shear stress. The size of the gelatin removed depends on the frequency of vibration and a release radius is defined. One way to achieve selective release of captured particles is by using a microtip device. Such a device for selectively releasing one or more captured particles in a gel, includes (1) a microtip; and (2) a vibrator mechanism that is connected to the microtip and moves the microtip at a controlled frequency, where the microtip when contacting the gel produces a localized shear stress in the gel at the controlled frequency, and releases one or more captured particles from the gel. The vibrator mechanism can consist of copper coil and cone mounted on a support, and magnets. The copper coil and cone are connected with an electricity source through connector.

A. EV Confocal Imaging

In some implementations, target EVs captured on the microfluidic device 110 can be directly imaged under a microcope. For example, micrographs of the microfluidic device 110 can be captured with an LSM510 confocal microscope (Zeiss, Peabody, Mass.) equipped with a 63x Zeiss Plan-APOCHROMAT® oil objective. Images are collected at the top plane of the device, i.e., top plane of the herringbone grooves. A total number of 100 images, e.g., 10 by 10 images in x- or y-axis, are acquired. In some instances, similar imaging parameters are used between samples to allow subsequent analyses. Images are processed using Zeiss microscope ZEN software. Semi-quantification of the captured EVs includes determining constant threshold of fluorescent intensity between the signal from EVs and noise and automatically calculated using imaging software.

B. RNA Isolation and Quantitative RT-PCR

In some implementations, biological cargo from captured target EVs, e.g., RNA, can be extracted for further analysis. In such implementations, isolated target EVs are lysed inside the microfluidic device 110 by pushing 700 µl Qiazol® through the device. RNA is subsequently extracted from lysates using the miRNeasykit (Qiagen, Valencia, Mass.). RNA is eluted from the columns in 50 µl water and concentrated by ethanol precipitation. RNA quality can be assessed using a 2100 Bioanalyzer® (Agilent Technologies, Santa Clara, Calif.) with an RNA 6000 Pico Chip kit (Agilent Technologies). Similar amounts of RNA were reverse transcribed using the VILO® super kit (Invitrogen, Carlsbad, Calif.). The relative levels of GFP, TdT, PPBP, EGFR, EGFRvIII, and GAPDH are assayed by single tube TaqMan® assays (Life Technologies, Carlsbad, Calif.): GFP, Mr00660654_cn; TdTomato, AI39R57; PPBP, Hs00234077_m1; GAPDH, Hs02758991_g1 [EGFRvIII].

C. Digital PCR

In some implementations, RNA extracted from isolated target EVs can be sequenced for amplification. In such implementations, RNA is reverse transcribed into 20 µl cDNA reactions using the Sensiscript Reverse Transcription Kit (Qiagen). Five µl of cDNA is used as input in duplicate reactions for each assay, e.g., EGFRvIII and EGFRwt. About 20,000 droplets are generated using an AutoDroplet® generator (Bio-Rad, Hercules, Calif.).

PCR conditions are as follows: 95° C.—10 min, 39 cycles at 94° C. for 30 sec and 61° C. for 1 min. The last stage is 98° C. for 10 min followed by 4° C. Droplets are analyzed using a Droplet Reader® (Bio-Rad). Gates are set to exclude all events from the cDNA no control template sample. All events above the no template control gates are considered positive. Concentrations are calculated in auto mode using software. The patient samples are run without knowing a priori which results from tissue or CSF biopsy are positive for EGFRvIII.

D. Library Preparation for RNA Sequencing

Target EVs are lysed with 700 µL of qiazol and RNA was extracted using a mRNAeasy kit form Qiagen (Hilden, Germany). RNA is amplified using an appropriate modification protocol and sequenced. Amplified cDNA is synthesized from the entire cell lysate using a SMARTer Ultra Low Input RNA Kit for Sequencing—v3 kit (Clontech Laboratories). PCR amplification following second strand synthesis is run for 18 cycles. One ng of amplified cDNA is loaded into the Nextera® XT kit. Normalization is done using the KAPA SYBR® FAST Universal qPCR Kit (Kapa Biosystems) rather than the bead-based normalization in the Nextera XT kit. The pooled libraries are sequenced on multiple lanes of a HiSeq2000.

E. RNA Sequencing Analysis

Data quality control from RNA sequencing is initially carried out using a throughput sequencer, for example, FASTQC, to generate a quality control report. Once samples are confirmed to have sufficient quality, samples are aligned to a reference genome using a RNA-seq aligner, such as the Spliced Transcripts Alignment to a Reference (STAR) aligner. Duplicate reads are marked using command line tools for manipulating high-throughput sequencing (HTS) data, such as PICARD, and removed using a suitable program, such as Samtools. Resulting stored sequence data, e.g., BAM files in .bam format, are used to quantify the read counts per gene using a suitable Htseq-count program.

Downstream analysis is carried out in a suitable programming language, such as R statistical programming language. To obtains insights into the sequencing data, 100, 500,1000 and 2000 most variant genes are selected for hierarchical clustering of all samples based on the expression of these genes. Differential expression analysis between the two clusters can be performed using a package, e.g., DESEQ2 package in R, to obtain a list of differentially expressed genes between any two conditions of interest. Heat maps can be plotted using, for example, a heatmap.2 function in gplots package in R.

F. Clinical Samples

As discussed above, different types of fluid samples can be used for capture and isolation of target EVs. In some implementations, blood is collected from healthy donors and patients having GBM. For example, a total of thirteen samples were collected from GBM patients and six healthy donors. Ten mL blood samples are collected by venipuncture into, for example, a BD Vacutainer SST tube (#367985) or a BD Vacutainer PPT® (#362788) for serum and plasma respectively. Samples are left to clot for 30 min at room temperature and processed within 2 hours of collection. Serum or plasma is then filtered through a 0.8 µm filter and run through the microfluidic device 110, as discussed above, or stored at −80° C. for later processing.

EXAMPLES

The invention is further described in the following examples, which do not limit the scope of the invention described in the claims.

Example 1

Antibody Selection and Engineering of Fluorescent EVs

A prototype of the microfluidic systems disclosed herein was developed to capture tumor-derived EVs derived from glioblastoma cell lines.

In this example, antibodies were selected based on surface markers highly expressed in glioblastoma cell lines, such as EGFR, EGFRvIII, EphA2, Podoplanin, PDGFR, and MCAM. Experiments were conducted using microfluidic devices that were functionalized with surface chemistries with different antibodies to evaluate capture efficiency of each antibody in capturing tumor-derived EVs. For these experiments, cell lines and fluorescent EVs were spiked into a human control serum and used to identify the most promising tumor-specific antibody candidates. Human Gli36 glioma cells were engineered to produce fluorescently labeled EVs to enable rapid, visual quantification of tumor-derived EVs during microfluidic optimization steps as discussed below. Specifically, Gli36 wild-type (Gli36 wt) expressing EGFR were infected with lentiviral vectors encoding PalmtdTomato, and Gli36 cells expressing EGFRvIII (Gli36-EGFRvIII) and EGFR were infected with lentiviral vectors encoding PalmGFP. The WT-plamdTomato and EGFRvIII-palmGFP fluorescent EVs are depicted in FIG. 3.

The fluorescent tumor-derived EVs were then spiked into human plasma or serum and processed through the microfluidic devices 110 depict in FIGS. 1B-D with channel surfaces functionalized with surface chemistries, as discussed above in reference to FIGS. 2A-B. Captured EVs were visualized by confocal microscopy and demonstrated the tunability of the systems depending on the antibody of choice. The specificity of antibody capture was tested by analyzing the binding of a mixed population of EVs to different antibodies.

Figure 4A:
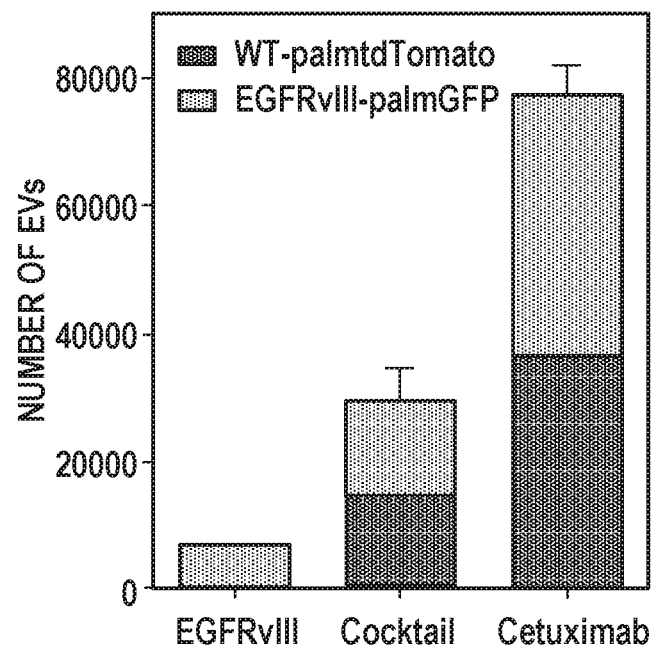
FIG. 4A is a graph depicting a comparison of capturing two fluorescently labelled EVs on a microfluidic device using different antibody solutions.

FIG. 4A is a bar graph depicting a comparison of capturing two fluorescently labelled EVs on microfluidic devices using different antibody solutions. As depicted, results showed that microfluidic devices coated with the EGFRvIII antibody mostly captured green-fluorescent EVs expressing EGFRvIII, while microfluidic devices coated with an antibody recognizing both EGFRwt and EGFRvIII (Cetuximab) captured both green- and red-fluorescent EVs. For EGFRvIII-specific antibody capture (i.e., EGFRvIII-PalmGFP EVs), the specificity of the device was 94.3%±0.6% (n=3 technical replicates, mean±s.e.m.). Moreover, an antibody cocktail directed against EGFR, EGFRvIII, podoplanin and PDGFR also exhibited capture affinity for both green- and red-fluorescent EVs.

Results also showed that, when using EVs that originated from parental cell lines with overexpression of EGFR and EGFRvIII, i.e., Gli36, a higher enrichment of tumor-derived EVs was achieved when Cetuximab alone was used (20 µm/ml used on-chip). For the cocktail of antibodies, the amount of Cetuximab bound on-chip was reduced by a factor of two (10 µg/ml) to allow for efficient placement of each antibody in the mixture. The resulting tumor-derived EV enrichment for Gli36 EVs was reduced by the same amount. When EVs from a cell line without EGFR overexpression was used (i.e., GBM 20/3), the cocktail of antibodies outperformed Cetuximab only.

Figure 4B:
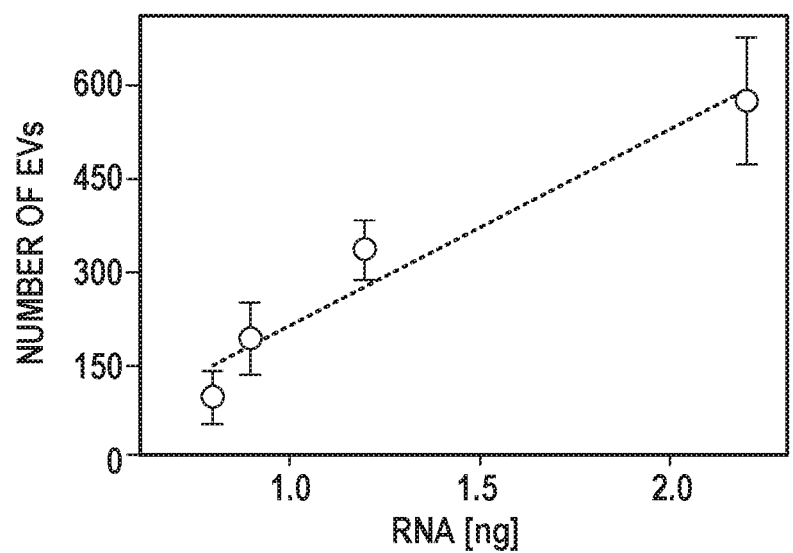
FIG. 4B is a graph depicting a correlation between a number of EVs captured on a microfluidic device and total RNA isolated from captured EVs.

Considering that the majority of assays for isolated EVs are molecular-based, the number of EVs imaged on the microfluidic device was then compared with the total mass of RNA extracted from the chip. FIG. 4B is a graph depicting a correlation between a number of EVs captured on a microfluidic device and total RNA isolated from captured EVs. The linear correlation between the two measurements ($r^2$=0.83) validated that the imaging-based approach disclosed herein was a reasonable surrogate for RNA-based analysis for efficient optimization during the development of microfluidic device design, as discussed above.

Figure 5A:
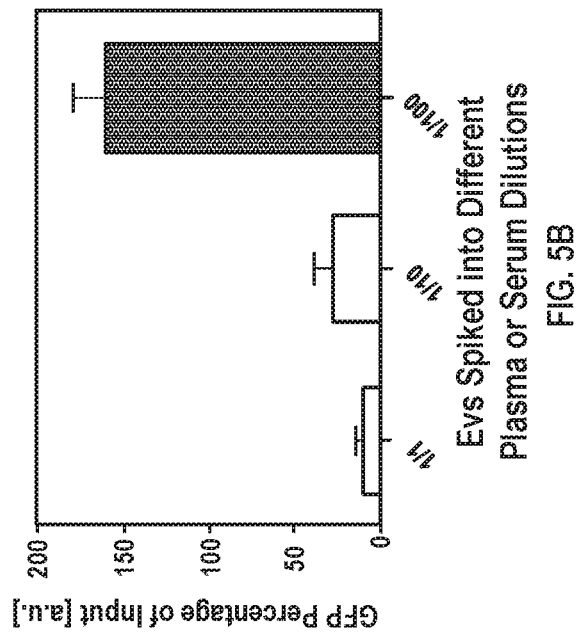
FIG. 5A is a graph depicting a comparison of capture efficiencies of EVs derived from glioblastoma multiforme (GBM) cell lines using different capture antibodies.

FIG. 5A is a bar graph depicting a comparison of capture efficiencies of EVs derived from GBM cell lines using different capture antibodies. In this experiment, different antibodies were selected to test specificity towards tumor-derived EVs for GBM cell lines, e.g., EVs from GBM20/3 cells. The results of the experiment were used to identify antibody candidates for the specific capture of tumor-derived EVs for GBM cell lines. Fluid samples were prepared by spiking respective antibodies in 1000 cell/ml solution in PBS. Of the different antibodies, microfluidic devices coated with Cetuximab and BAF antibodies had the highest capture efficiencies of target EVs.

Figure 5B:
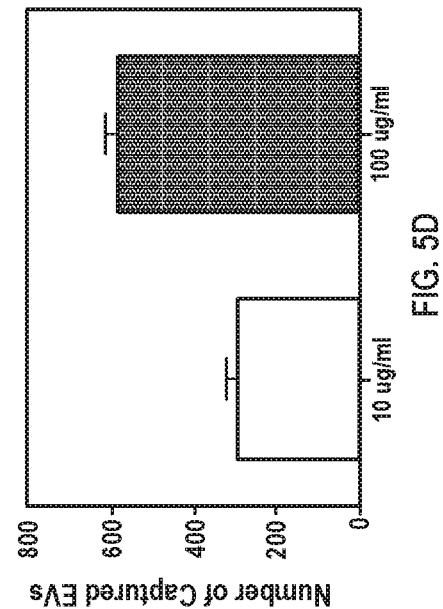
FIG. 5B is a graph depicting a comparison of tumor-specific messages for EVs derived from GBM cells spiked into serum or plasma at different dilution ratios.

FIG. 5B is a bar graph depicting a comparison of tumor-specific messages for EVs derived from GBM cells spiked into serum or plasma at different dilution ratios. In this experiment, EVs from GBM20/3 palmGFP cells were spiked into plasma to quantify tumor-specific message at dilution ratios of 1:1, 1:10, and 1:100. Liquid samples with the different dilution ratios were then flowed in the microfluidic devices. Once captured, target EVs were lysed to isolate and extract RNA from the target EVs. The extracted RNA was analyzed using TaqMan assay for GFP. The percentage of GFP in the extracted RNA was used as an indicator of capture efficiency. Results indicated that 1:100 was the dilution ration with the highest level of GFP percentage of input, which represents the optimal dilution ratio for spiking EVs into liquid samples.

Figure 5C:
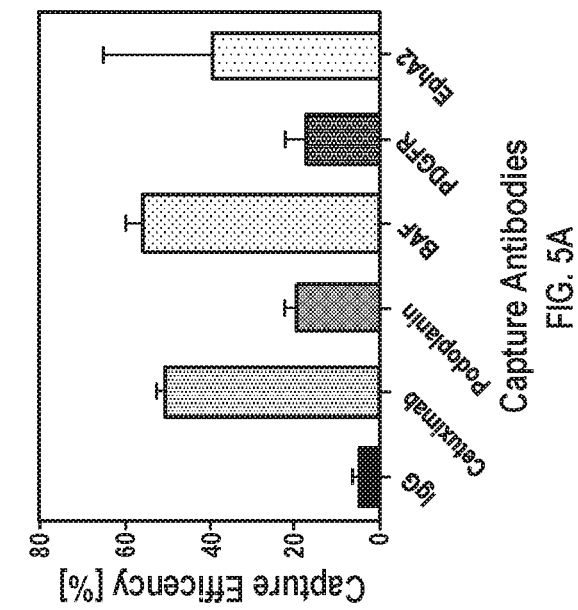
FIG. 5C is a graph depicting a comparison of obtained enrichment ratios at different stages of sample processing using a microfluidic device.

FIG. 5C is a bar graph depicting a comparison of obtained enrichment ratios at different stages of sample processing using a microfluidic device. In this experiment, the tumor-derived EV transcript (EGFRvIII) and a general EV transcript (glyceraldehyde 3-phosphate dehydrogenase, GAPDH) were evaluated using a TaqMan® Gene Expression assay to compute an enrichment ratio metric. The enrichment ratio metric was computed at different stages of sample processing, e.g., input, microfluidic device, eluate, and control, to confirm that total detected RNA was due to specific binding of tumor-derived EVs and not due to non-specific binding of EVs to the surface. Results showed a statistically significant increase in enrichment at the microfluidic device stage (n=3 technical replicates; ±s.e.m., *, ** p<0.05, 1-way ANOVA).

Figure 5D:
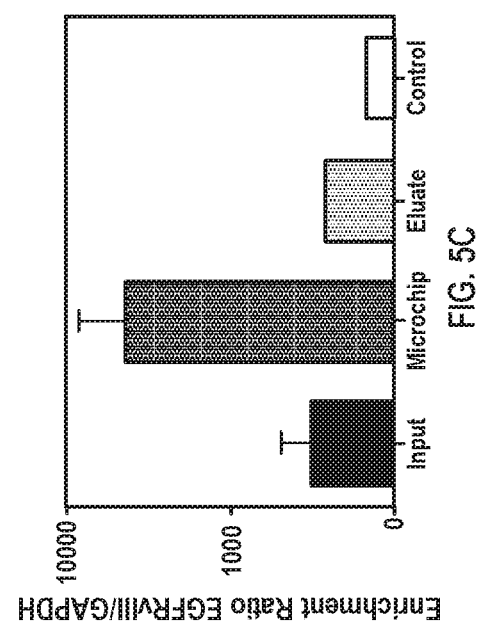
FIG. 5D is a graph depicting an effect of antibody dilution on tumor-derived EV capture.

FIG. 5D is a bar graph depicting an effect of antibody dilution on tumor-derived EV capture. In this experiment, microfluidic devices were coated with antibody solutions with concentrations 10 µg/ml and 100 µm/ml to evaluate the effect of antibody concentration on capture efficiency of target EVs. Results showed that the 100 µm/ml concentration caused a statistically significant increase in capturing target EVs (n=3 technical replicates; ±s.e.m., *p<0.05, student t-test).

These results demonstrate the high degree of specificity for capturing target EVs using the microfluidic devices. Additionally, maintaining (and sometimes improving) performance with increased dilution of EVs is strongly suggestive that the technique can be used for isolation of EVs that are present at very low (<1%) concentrations in bodily fluids, e.g., serum, plasma, blood, urine, CSF, breast milk, tears, saliva.

Example 2

Processing Conditions

Antibody-based capture in microfluidic devices is often sensitive to processing conditions. As such, experiments were conducted to evaluate the impact of processing conditions on EV isolation on the microfluidic devices, as described above (results not shown).

The impact of flow rate on EV capture was initially evaluated using tumor-derived EVs spiked into human serum or plasma. EV Capture was characterized by the percentage of RNA collected in the microfluidic devices. Fluid samples were flowed through microfluidic devices at flow rates of 0.5, 1, 2, and 5 mL/h.

Results showed that varying the flow rate of the fluid changed the number of captured EVs. Specifically, at flow rates below 1 mL h/l, more EVs were captured, as indicated by a high amount of RNA obtained (24.3%±2.3%). As the flow rate was increased to 2 mL h/l or higher, the total amount of RNA dropped by 88%.

To quantify if these total RNA amounts were specific to the isolation of tumor-derived EVs or due to non-specific binding of EVs to the surface, the tumor-derived EV transcript (EGFRvIII) and a general EV transcript (glyceraldehyde 3-phosphate dehydrogenase, GAPDH) were evaluated using a TaqMan® Gene Expression assay to compute an enrichment ratio metric. While flow rates below 1 mL h/l resulted in the maximum yield of RNA, the highest enrichment ratio for tumor-derived RNA was achieved at 1 mL/h. A flow rate of 1 mL/h therefore allows for 1 mL of plasma to be processed through the entirety of the assay (inclusive of all wash steps and RNA extraction) in less than 3 hours.

The tumor-derived EV capture performance of the microfluidic devices was then compared against bulk EV analysis (i.e., ultracentrifugation) of the input samples and eluates, or "waste" of the microfluidic devices. Based on these tests, microfluidic devices demonstrated a tumor-derived EV capturing specificity with more than a 10-fold enrichment of EGFRvIII transcripts. Additionally, the specificity of the enrichment was tested at different dilutions, which still showed better performance than ultracentrifugation.

Example 3

Effect of Linker Molecule Length on Capture Efficiency

As discussed above, surface chemistry including layers of gelatin, nanostructured substrates, and flexible elongated linker molecules can be used to functionalize channel surfaces of microfluidic devices with binding moieties, such as antibodies specific to target EVs. The effect of the length of separation between antibodies and the nanostructured substrates, i.e., linker molecule length, on target EV capture was evaluated to identify the length for the flexible linker molecules that maximized capture efficiency.

Figure 6:
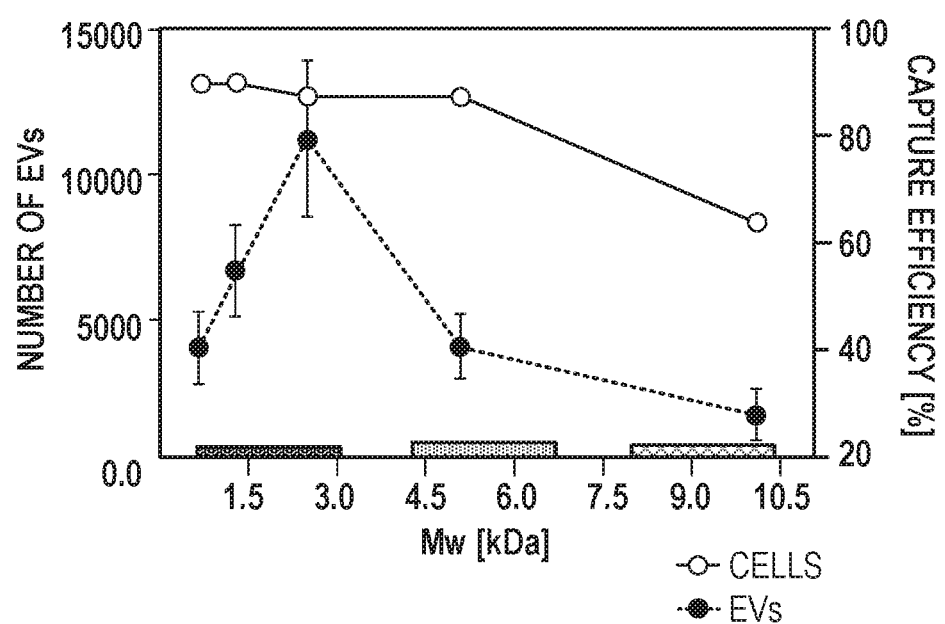
FIG. 6 is a graph depicting effect of linker size on cell and EV capture on microfluidic devices.

FIG. 6 is a series of graphs depicting the effect of linker molecule size on cell and EV capture on microfluidic devices. The size of linker molecules was almost negligible to capture efficiency for micrometer-sized cells. Specifically, for molecular weights ranging from 0.6 to 5 kDa, the capture efficiency for cells ranged from 93±2.4 to 92±1.8% respectively. A decrease in capture efficiency to 63±2.1% was found when the molecular weights were increased to 10 kDa.

A different profile of capture efficiency was observed for EVs with different linker molecules. Specifically, for molecular weights between 0.6 to 2.4 kDa, there was a proportional increase in the number of Gli36 wt PalmtdTomato EVs captured on the surface of the microfluidic devices. However, molecular weights greater than 2.4 kDa, e.g., 5, 10, 15, 20 kDa, showed a decrease in the number of captured EVs.

Further experiments were conducted to measure Zpotential as an indication of specific binding. Results of these experiments showed that EVs bound to an antibody linked to a PEG chain significantly decreased the Zpotential of the total complex formed, which was an indication of specific binding. A PEG linker of 2.4 kDa showed a proximity to zero Zpotential and also exhibited the greatest capture efficiency. Thus, a 2.4 kDa molecular weight likely represent an optimal configuration for the flexible linker molecules when integrated with the microfluidic devices for EV capture.

Example 4

Nanoparticle Distribution Across Surfaces of Microfluidic Devices

Figure 7:
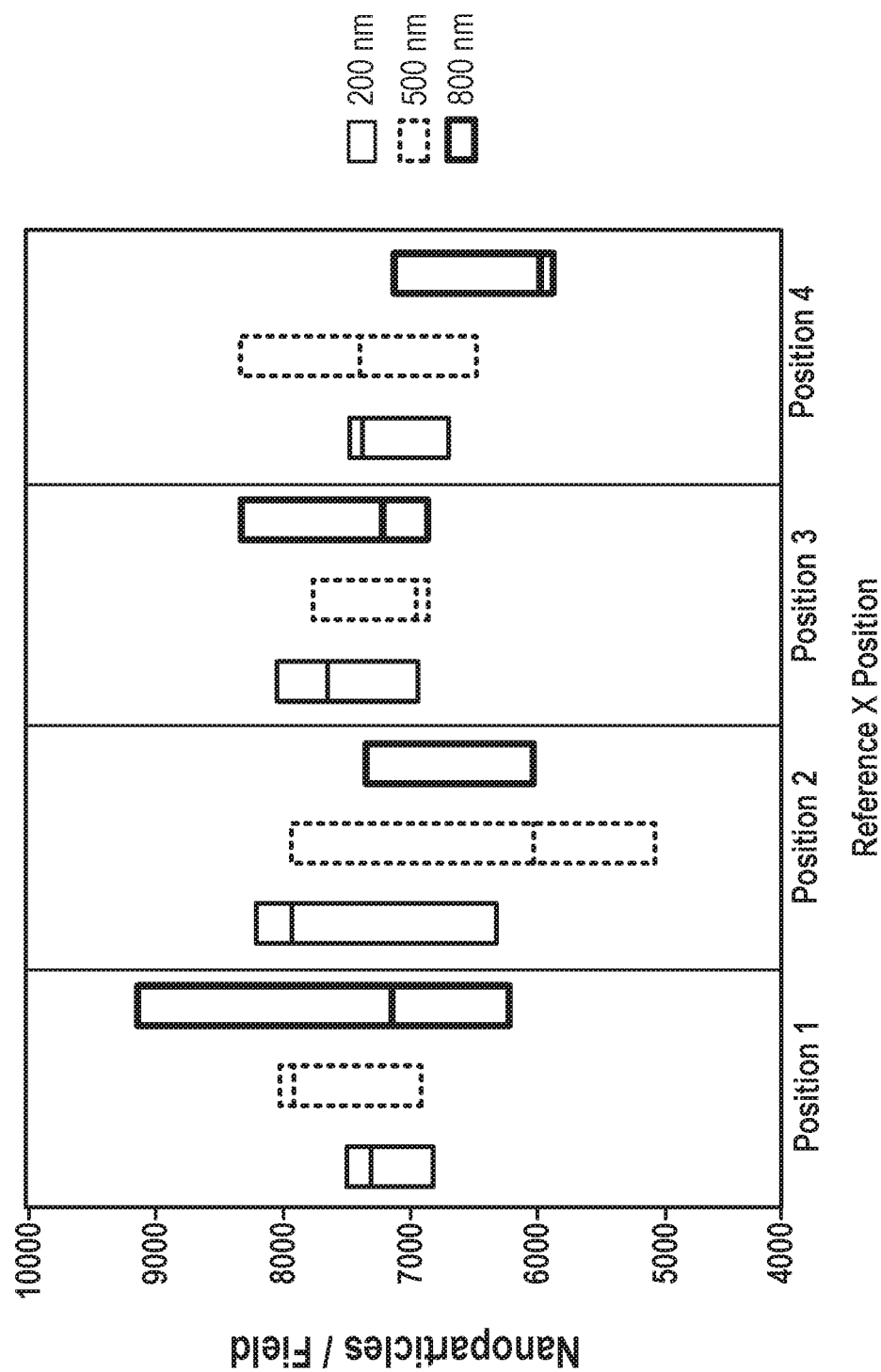
FIG. 7 is a graph depicting a characterization of captured nanoparticles across surfaces of microfluidic devices.

The ability of the microfluidic devices to capture tumor-derived EVs without size-bias was evaluated by characterizing captured nanoparticle distribution across the surfaces of the microfluidic devices. A mixture of biotinylated-nanoparticles of different sizes was initially spiked in plasma ($5 \times 10^9$ particles mL) and was run through the microfluidic devices at a flow rate of 1 mL/h. FIG. 7 is a graph depicting a characterization of captured nanoparticles across surfaces of microfluidic devices. As shown, regardless of size, e.g., 200, 500, 800 nm, EVs were captured across the length of the device microfluidic with no significant differences ($p > 0.05$, 1-way ANOVA). The size distribution of EVs isolated from Gli36 cells pre- and post-microfluidic device capture was evaluated by a tunable pulse resistive sensing (TPRS) method and showed that different populations of EVs were present on the microfluidic devices.

Example 5

Specific Capture of Target EVs

Experiments were conducted to investigate ways to increase the specific capture of tumor-derived EVs. Results of these experiments showed that running liquid samples containing EVs or cells through a depletion chip, e.g., a microfluidic device coated with control IgG, before running the fluid samples through a functionalized chip, e.g., a microfluidic device coated with specific antibodies, increased specific capture by 15%. The increase in capture was found not to be dependent on the antibody in the depletion chip since a blank chip, e.g., a microfluidic device with no antibody coatings, also increased specific capture in the functionalized chip. As discussed above in reference to FIG. 1A, this increase in capture is due to depletion of non-target EVs (e.g., EVs from platelets) at the first chip, which then increases specific binding of target EVs with antibodies coated on the second chip. Additional experiments were then conducted to show that the IgG chip does not deplete the tumor-derived EVs by quantifying the changes in EV concentration before and after flowing EVs spiked in PBS through the device. Results showed that less than 5% of the EVs remained on the IgG-coated device. Additionally, PCR analysis indicated that the IgG-coated device captured 10-fold fewer EVs in comparison to the EVHB-Chip coated with tumor-specific antibodies.

Experiments were conducted to determine whether the surface of microfluidic devices were saturated by running a liquid sample through multiple microfluidic devices in series, i.e., running a fluid sample initially through a first microfluidic device, and running a portion of the fluid sample exiting through an outlet of the first microfluidic device through a second microfluidic device. In these experiments, multiple dilutions of targets EV in plasma were run through five microfluidic devices and tested for binding to surfaces of the microfluidic devices. Once captured, target EVs, e.g., GBM20/3-GFP EVs, were lysed to isolate and extract RNA from the target EVs. The extracted RNA was analyzed using TaqMan assay for GFP. The percentage of GFP in the extracted RNA was used as an indicator of capture efficiency. Additionally, a ratio of measured GFP and PPBP levels in the extracted RNA was used as an indicator of enrichment level.

Figure 8A:
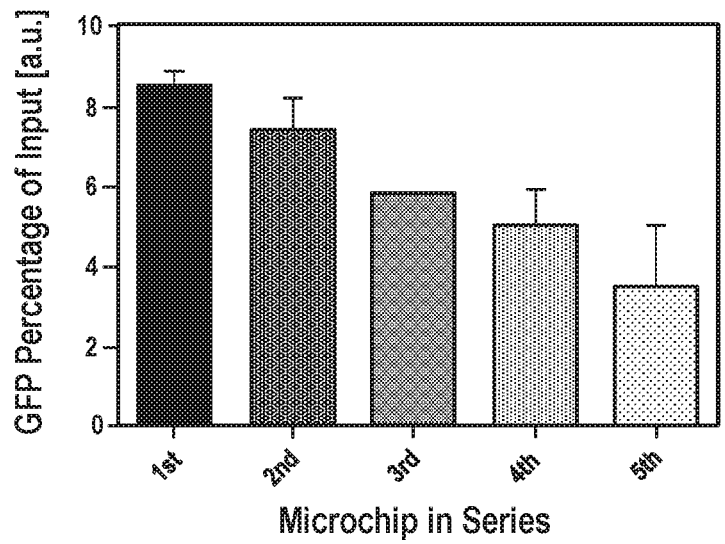
FIG. 8A is a graph depicting measured capture efficiency of target EVs on the surfaces of five microfluidic devices that are run in series.

FIG. 8A is a bar graph depicting measured capture efficiency of target EVs on the surfaces of five microfluidic devices that are run in series. These results indicate depletion on the number of EVs between the first and second microfluidic devices at different dilutions (not shown), which suggested that the first microfluidic device was saturated.

Figure 8B:
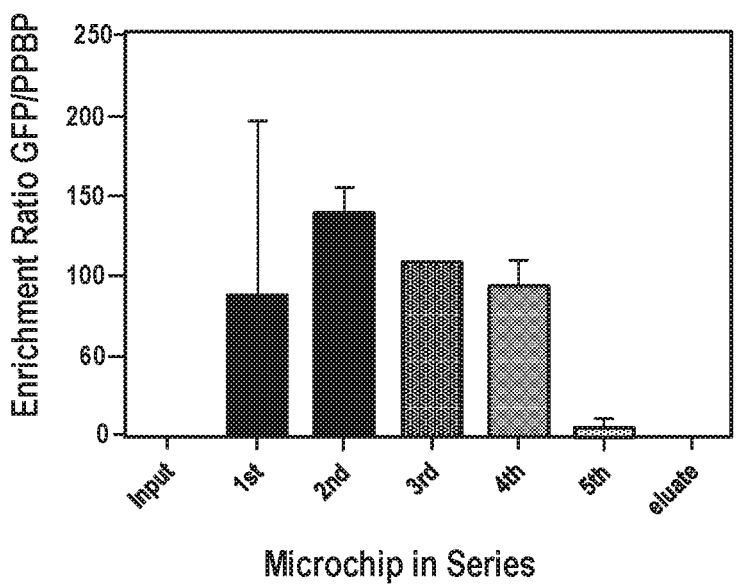
FIG. 8B is a graph depicting enrichment levels of target EV capture on the surfaces of five microfluidic devices that are run in series.

FIG. 8B is a bar graph depicting measured enrichment levels of target EV capture on the surfaces of five microfluidic devices that are run in series. When each microfluidic device was analyzed individually, the highest capture efficiencies were observed in the first and second microfluidic devices and a gradual decrease in capture in the subsequent microfluidic devices. The GFP/PPBP enrichment ratio was relatively stable over the first four microfluidic devices run in series, which indicated that target EVs were captured with relatively high specificity. However, a significant drop of 92% of the GFP/PPBP enrichment ratio was observed in the 5th EVHB-Chip (p<0.05, student-t-test, between fourth and fifth microfluidic devices).

The results from the experiments discussed above indicated that the most efficient target EV capture was obtained by running four functionalized microfluidic devices in series after a blank microfluidic device. This experimental setup was therefore used in evaluation of target EV capture from clinical samples.

Figure 9A:
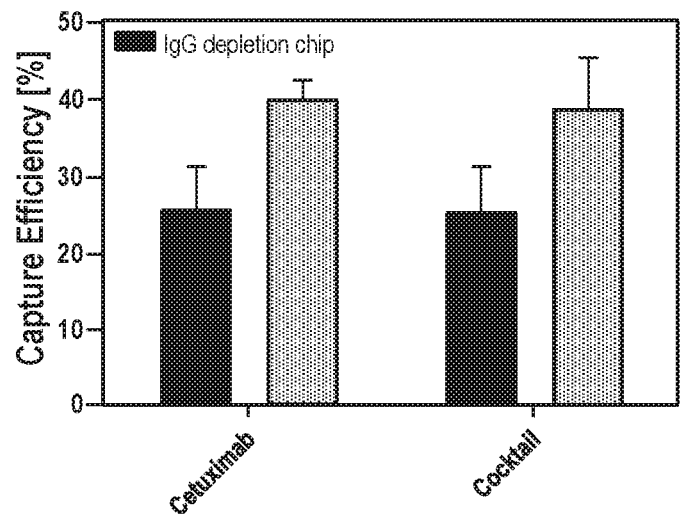
FIG. 9A is a graph depicting a comparison of EV capture across a surface of a single microfluidic device and EV capture using two microfluidic devices that includes a microfluidic device coated with control IgG.

Additional experiments were then conducted to compare the efficiency of capturing target EVs using a single microfluidic device and capturing target EVs using two microfluidic devices, of which the first was a depletion chip as discussed above. FIG. 9A is a bar graph depicting a comparison of EV capture across a surface of a single microfluidic device and EV capture using two microfluidic devices that includes a microfluidic device coated with control IgG. In this experiment, target EVs, e.g., GBM20/3 PalmGFP EVs, were captured using a single chip setup (black bars) and a dual chip setup (grey bars), and using two antibody solutions. With respect to the dual chip setup, the first chip was coated a control IgG, whereas the second chip was coated either with Cetuximab or an antibody cocktail directed against EGFR, EGFRvIII, podoplanin, and PDGFR. As shown, the dual chip setup resulted in higher capture efficiencies compared to the single chip setup. Moreover, capture efficiency of the different antibody solutions was comparable, which indicates that the differences in capture efficiencies between the way in which the microfluidic devices were run, e.g., single chip setup or dual chip setup, was not likely attributable to use of a specific antibody solution.

Figure 9B:
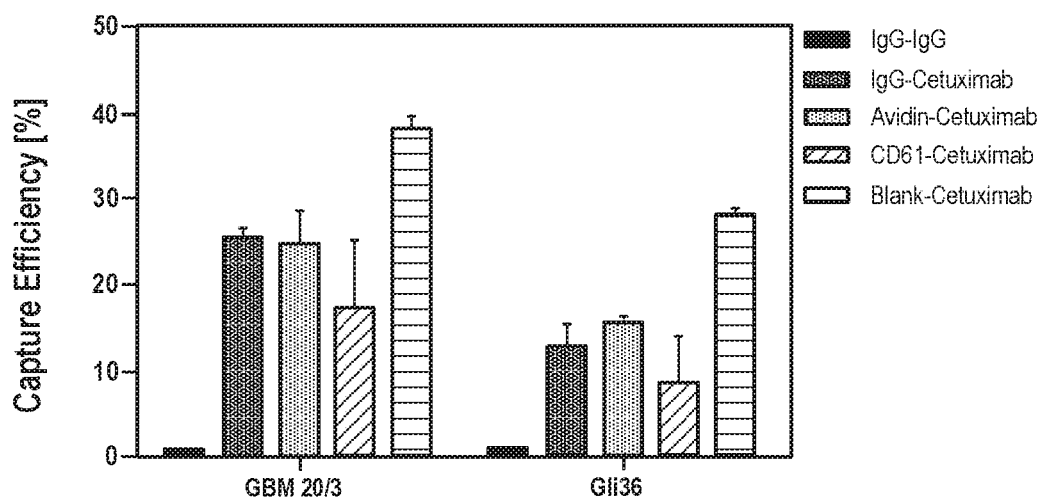
FIG. 9B is a graph depicting a comparison of capture efficiencies of target EVs cells run through two microfluidic devices in series with different antibody surface chemistries.

Experiments were then run to evaluate the capture of two target EVs, e.g., EVs from GBM20/3 cells and Gli36 cells, using a dual chip setup and with respect to different control antibody surface chemistries. FIG. 9B is a bar graph depicting a comparison of capture efficiencies of target EVs cells run through two microfluidic devices in series with different antibody surface chemistries. In this experiment, the first chip was coated with different control antibody solutions, such as IgG-IgG, IgG-Cetuximab, Avidin-Cetuximab, CD61-Cetuximab, and Blank-Cetuximab. Capture efficiency of the two target EVs were then measured at the second chip. Results showed similar results for capture efficiency between the antibody solutions with respect to the two target EVs. Specifically, use of the Blank-Cetuximab control antibody solution in the first chip resulted in highest capture efficiencies in the second chip for both target EVs from GBM20/3 and Gli36 cell lines. In contrast, use of the IgG-IgG control antibody solution resulted in the lowest capture efficiencies.

Example 6

Capture Efficiency and Limit of Detection Studies

Following testing of the microfluidic systems at three different levels, e.g., device processing conditions, capture antibodies, releasable nano-interface coating, experiments were conducted to determine target EV capture efficiency and limits of detection of the microfluidic devices. For target EV capture efficiency, a known number of EVs, e.g., concentrations between 35 to 50 million of particles per mL of PBS were used, were spiked into a solution. The spiked solution was then flown through the microfluidic devices. The concentration of EVs in the flowed solutions was analyzed before and after the samples were run through the microfluidic devices to determine how many EVs were depleted from the sample. Results of these studies indicate a capture efficiency of 58.77±5.37 (mean±s.e.m.) for the microfluidic devices.

The limit of detection was calculated using the average fluorescence intensity of captured target EVs. For these experiments, a series of dilutions of spiked EVs in PBS were prepared from a known stock concentration. Then, the EVs captured on the microfluidic devices were imaged on a fluorescent microscope with the same exposure times for all the different titration conditions. It is important to mention that individual EV fluorescence was not measured. The nanoparticle layer deposited on the surface of the microfluidic device aggregates the EVs on the surface allowing them to be visualized and quantified at a bulk level. The aggregation of EVs has been shown to be appropriate to quantify limits of detection. The current limit of detection was identified as 100 EVs/µL.

Example 7

Captured Target EV Extraction Studies

As discussed above, once target EVs have been captured using the microfluidic devices, techniques can be used to release the captured target EVs from channels of the microfluidic devices for extraction and downstream processing. Experiments were conducted to characterize both capture and release target EVs from the surfaces of the microfluidic devices.

Figure 10A:
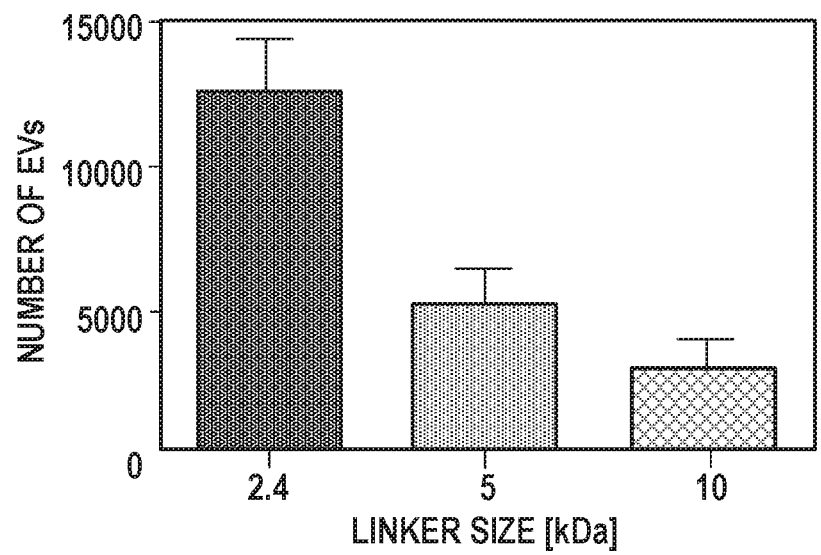
FIG. 10A is a graph depicting a comparison of EV capture on the surface of a microfluidic device for different linker molecule sizes.

FIG. 10A is a bar graph depicting a comparison of EV capture on the surface of a microfluidic device for different linker molecule sizes. In this experiment, capture of target EVs, e.g., PalmtdTomato EVs, was quantified using microfluidic devices that were coated with different surface chemistries, e.g., different sized linker molecules bound to nanostructured substrates as discussed above. Results showed that microfluidic devices that were coated with linker molecules having molecular weights of 2.4 kDA had the highest capture efficiency, with capture efficiency reducing with increasing molecular weights from 5 kDa to 10 kDa.

As discussed above, two techniques can be used to release target EVs that have been captured on microfluidic devices. First, EVs can be eluted from the surface of the microfluidic devices by flushing a proteinase K solution (0.05%) that shaves EVs from the device. Second, a thermally responsive gelatin nanocoating can be selected as the base layer for nanoparticles to be attached to the microfluidic devices, as discussed above. At room temperature, the gelatin nanocoating is highly stable but when the temperature of the microfluidic devices is raised to physiological temperature, e.g., 37° C., the coating dissolves within seconds, releasing all captured EVs. To test the success of EV release using proteinase K captured EVs were released from the surface of the device and subsequently quantified by confocal microscopy.

Figure 10B:
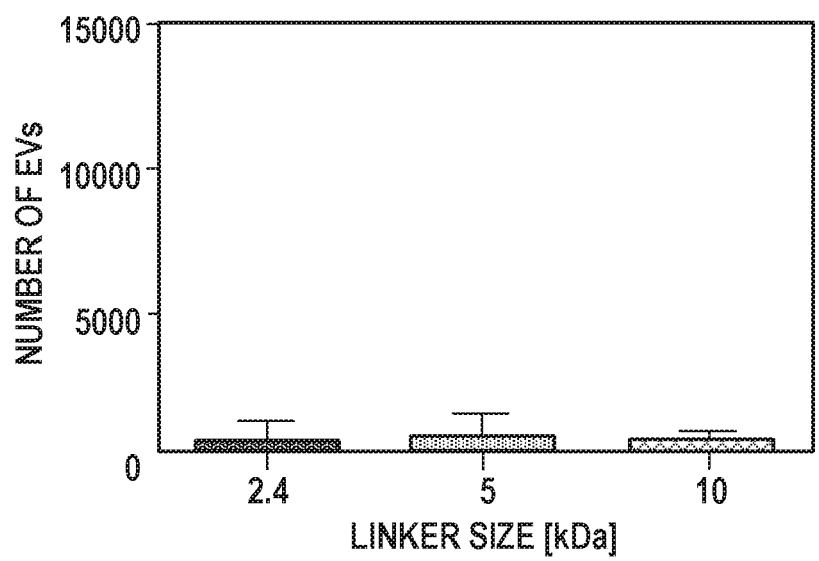
FIG. 10B is a graph depicting a comparison of capture of EVs remaining on the surface of a microfluidic device after extraction using different linker molecule sizes.

FIG. 10B is a bar graph depicting a comparison of capture of EVs remaining on the surface of a microfluidic device after extraction using different linker molecule sizes. In this experiment, captured target EVs were measured on microfluidic devices with different sized linker molecules after the procedure to extract the captured target EVs, e.g., through elution or by increasing the temperature, had been performed. Results showed that, regardless of the size of the linker molecule used, approximately 87% of captured target EVs were removed from the surface of the microfluidic devices after extraction procedures were performed, i.e., approximately only 13% of captured target EVs were not extracted from the microfluidic devices once the extraction procedures were performed.

Example 8

Comparison to Standard EV Isolation Methods

Once design of the microfluidic devices was evaluated and optimized, as discussed above, EV capture and isolation performance of the microfluidic devices were compared to that of standard EV isolation techniques, such as ultracentrifugation and magnetic bead separation. In these examples, samples of target EVs, e.g., PalmGFP-EGFRvIII GBM EVs, were spiked into plasma were divided in triplicates and run independently on each platform. Samples used to evaluate ultracentrifugation were centrifuged for 2 hours at 100,000× g. Samples used to evaluate magnetic separation were incubated with 3 µm magnetic, antibody-coated, polystyrene beads for 2 hours. Samples used to evaluate the microfluidic devices were run for the same amount of time as discussed above. For all three platforms, isolated EVs were lysed and homogenized with 700 ‖L of Qiazol buffer. Quantification of the tumor EV-specific message (GFP) indicated that the microfluidic platform had a 10-fold higher GFP mRNA content compared to ultracentrifugation and bead-based separation methods.

Figure 11A:
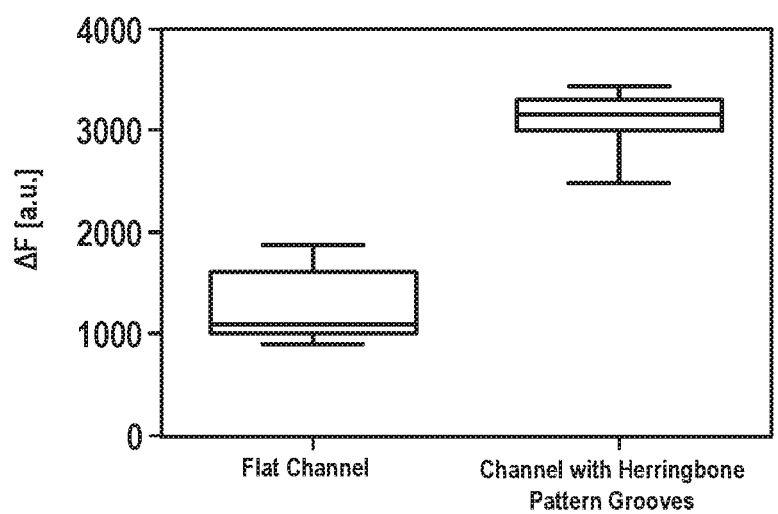
FIG. 11A is a graph depicting a comparison of average fluorescence intensity measured for EVs captured on a microfluidic flat channel and a channel with herringbone pattern grooves.

Further experiments were conducted to characterize the benefit gained from using herringbone pattern grooves of the microfluidic devices. In these experiments, tumor-derived EV capture in a flat channel microfluidic device was compared to capture in a device of the same dimensions but with staggered herringbone groves in the ceiling of the device (with all other parameters held constant). FIG. 11A is a graph depicting a comparison of average fluorescence intensity measured for EVs captured on a microfluidic flat channel and a channel with herringbone pattern grooves. FIG. 11A shows that the addition of herringbone structures resulted in approximately a 60% increase in the target EV capture.

Figure 11B:
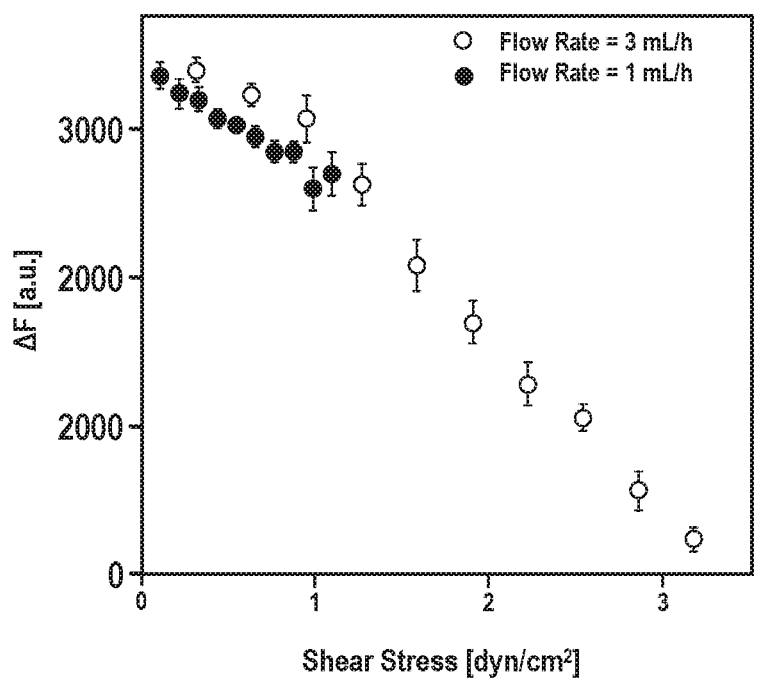
FIG. 11B is a graph comparing shear stress measured in a Hele-Shaw device using two flow rates.

The impact of shear stress resulting from different flow rates on EV capture was also investigated. The shear stress that was most favorable for antibody binding of EVs at different flow rates was also calculated based on these results. FIG. 11B is a graph comparing shear stress measured in a Hele-Shaw device using two flow rates, 1 mL/h and 3 mL/h. A Hele-Shaw device in which the shear stress along the axis of the chamber decreases linearly along the chamber length without changing the input flow rate was used. At 1 mL/h, the shear stress experienced by the target EVs was 0.11 to 1.1 dyn/cm$^2$ with a drop of 19.6% in the fluorescence intensity of captured EVs, between the lowest to highest points of shear stress. When the flow rate was increased to 3 mL/h, the resulting shear stress was calculated to be between 0.32 to 3.17 dyn/cm$^2$ with a 92.8% decrease in the fluorescence intensity, indicating a marked decrease in EV capture at these shear stresses.

Additionally, because not all EV assays are based on molecular analysis, it is important to highlight that the size and optical transparency of the microfluidic devices is highly suitable for visualization of EVs by immunoaffinity staining on-chip. To accomplish this, EVs from a human glioma cell line Gli36 were captured on the microfluidic devices and subsequently labeled using an anti-EGFR antibody and a fluorescent secondary antibody. This technique enabled visualization of the fluorescent signal produced by the captured EVs at the surface of the microfluidic devices.

Example 9

Molecular Profiling of Tumor-Derived EVs from GBM Patients

As discussed above, in some implementations, the systems and techniques disclosed herein can be used to capture, isolate and investigate tumor-derived EVs from glioma cell lines from fluid samples of patients with GBM. In GBM, a high degree of intra-tumor heterogeneity can complicate the genetic analysis of biopsy samples, and important oncogenes like EGFRvIII that promotes tumor formation by activating aberrant signaling and epigenetic pathways, can have a variable expression pattern within the tumor. Therefore, tumor-derived EVs released into the blood stream may provide a more accessible and representative source of biomarkers, potentially providing real-time information regarding tumor response and subsequent evolution in response to treatment.

Experiments were conducted using samples collected from a group of thirteen patients and six healthy patients. The experiments were then used to test the clinical utility of the microfluidic systems and techniques disclosed herein. In some parallel experiments, tissue and cerebrospinal fluid (CSF) biopsies of six patients were performed for molecular profiling, including positive evaluation for the EGFRvIII mutation in 3 of 6 of the tumor samples. The biopsies and CSF samples showed a significant variability in the EGFRvIII analysis, with only one patient (Pt3) demonstrating EGFRvIII positivity in both CSF and tumor tissue.

EVs were isolated from fresh and banked GBM patient serum (n=2) or plasma (n=11) using the microfluidic devices, with 2 mL of sample tested for each patient. To gain insight into the capture efficiency for these clinical samples, the fluid that entered and exited the microfluidic devices was also collected and ultracentrifuged to isolate the EVs. For the patient samples whose EGFRvIII status was known (n=6), samples were analyzed in duplicate for the presence of EGFRvIII RNA using digital droplet PCR (ddPCR).

The presence of EGFRvIII signal derived was initially quantified from the target EVs captured on the microfluidic devices and compared to the values obtained from ultracentrifugation of the same sample before and after processing with the microfluidic devices. Tumor-derived EVs were isolated using the microfluidic systems coated with a cocktail of antibodies, that included anti-Cetuximab, anti-Podoplanin, anti-PDGFR, anti-EGFRvIII, andti-BAF. The tumor-derived EVs were lysed and RNA was extracted directly from the microfluidic devices. Droplet digital PCR was used to quantify EGFRvIII and levels were normalized to total samples inputted. Values were expressed as absolute copy numbers of EGFRvIII mRNA. The levels of EGFR WT were also quantified for the six patients and the health controls.

Figure 12A:
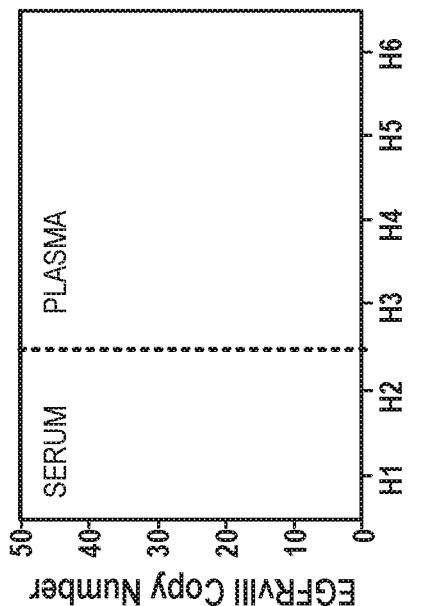
Figure 12B:
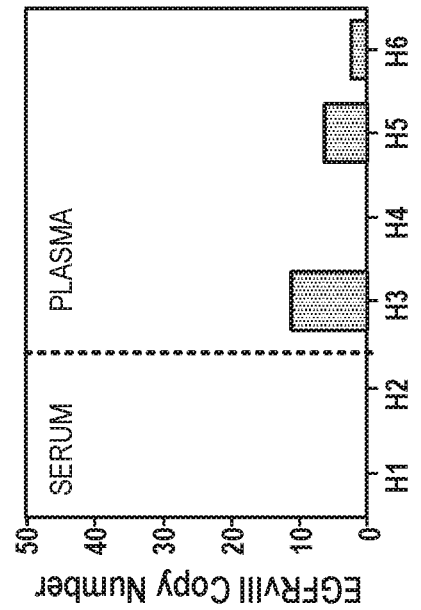

FIGS. 12A-D are a series of bar graphs depicting a comparison of EGFvIII mRNA quantification in serum and plasma-derived EVs using droplet digital PCR on patient samples. FIGS. 12A and 12B depict EGFvIII mRNA levels that were quantified at the mRNA from six GBM patients and six healthy control patients, respectively. Analyzing similar volumes for each of the conditions, the results showed that the number of positive droplets, or EGFRvIII events, was significantly less for the ultracentrifuged samples before and after the device. As an example, for patient six, the average number of EGFRvIII positive events for the input was 1, 3 for the outlet, and 53 for the microfluidic devices (n=2). The housekeeping gene (GAPDH) was used to determine the degree of non-specific background RNA message present in the samples (inlet, outlet, and EVHB-Chip), with a similar comparison demonstrating markedly higher GAPDH RNA positive events in the ultracentrifuged samples (input: 1857; output: 1696; microfluidic device: 236, n=2). These results indicated that EVs isolated from the microfluidic devices yield much higher levels of tumor-specific RNA (EGFRvIII), while having significantly less background RNA from not-tumor EVs (GAPDH).

Figure 12C:
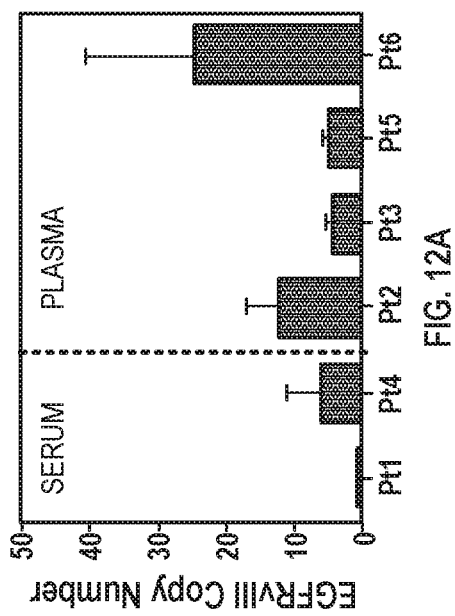
Figure 12D:
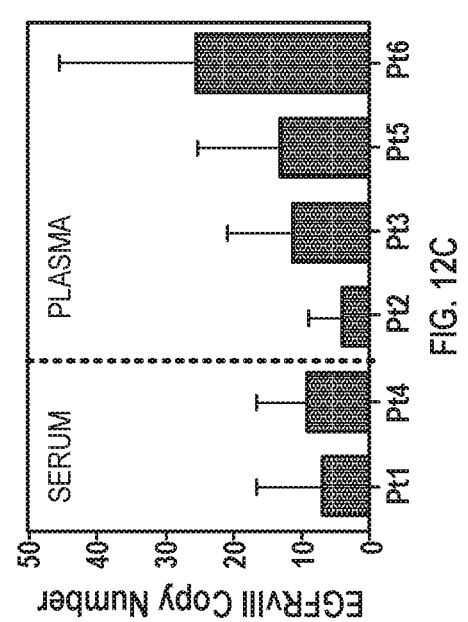

Using the GBM patient samples, the microfluidic devices demonstrated high specificity for the EGFRvIII mutation in patients as zero levels were found in our age-matched control samples (as shown in FIGS. 12A and 12B). While the number of events positive for the EGFRvIII varied across patients, 5 out 6 patients exhibited EGFRvIII mRNA transcripts. Additionally, total wild-type EGFR signal levels were compared by ddPCR, and data indicated that more RNA copies were captured on the chip in most patients as compared to control samples (as shown in FIGS. 12C and 12D). When comparing against the traditional biopsy methods for EGFRvIII detection, the results matched at least one of the biopsy methods (CSF or surgical biopsy) for three patients. The other three patients were positive for EGFRvIII only by the microfluidic devices.

For all patient samples, the EVs captured on the microfluidic devices were then analyzed for the presence of characteristic GBM expression signatures by using an amplified RNA sequencing protocol designed for minute quantities of material. FIG. 13 is a representation of heatmaps of RNA of EVs isolated using the microfluidic devices.

FIG. 13 shows that unsupervised clustering analysis of the top one hundred most variant genes showed distinct cluster separation between patients and healthy controls (a.—plasma samples (n=11 patients and 4 controls); b.—serum samples (n=2 patients and 2 controls)). Many of the patient samples were obtained prior to the initial tumor biopsy, when the official tumor classification was unknown. Upon analysis of the biopsy specimen, patient 11 was determined to be an anaplastic oligodendroglioma (AO). While the sample number is too low to draw any conclusions, it is interesting to note that this AO sample clusters separately from our glioblastoma patients and healthy donors. Lastly, differential expression between EV isolated using ultracentrifugation and the microfluidic devices demonstrated marked changes, indicating that these two methods result in the isolation of distinct populations of EVs.

Comprehensive characterization of GBM EV RNA was then performed for the studied patient samples. For the six GBM samples that were analyzed for EGFRvIII mutational status, a total of 54 GBM genes from a database of primary tumors were detected in tumor-derived EV transcriptomes. Genes previously associated with patient survival (e.g. MAST3, LRRTM2, PEXSL, GADD45A), disease progression (e.g. ACSL4, AMFR, ARHGEF7, BASP1, EHMT2, MAP3K1, MLLT1, CD151, CDC14B, E2F3), tumor resistance to radiotherapy or chemotherapy (e.g. ABBC3, PTPRC, ACTN1, EI24, LCN2), and genes related to stem cell function and putative tumor evolution from a primary or secondary glioblastoma (e.g. CDKN1A, ID1, and ID3) were identified. Notably, commonly mutated genes for GBM were found over-represented and were grouped as signaling genes (e.g. KRAS, NUCB1, PIK3CA, PRKAR1B). Moreover, gap junction protein and angiogenesis genes showed an over-represented in the cohort of patients (gap and tight junctions: GJC1, CLDN5; angiogenesis: CXCL5, GUCY1A3, GUCY1B3). Also, 38 cancer-associated genes were identified that were not previously reported in EVs from GBM patients.

Finally, using available databases of genes, sets of genes uniquely present in each of the four characteristic GBM subtypes were complied. Then, an unsupervised cluster analysis was performed for these gene signatures of EVs isolated from the microfluidic device for patients and healthy controls. More than 40 genes were identified per subtype that have at least two of their respective landmark genes. For classical subtype: PDGFA, EGFR, and AKT2, for neural subtype: FBXO3, GABRB2, MBP; for proneural subtype: SOX2, ERBB3; for mesenchymal subtype: TLR4, RELB, PTPRC, and CASP1/4/8. These results demonstrate that the microfluidic devices captured tumor EVs containing GBM enriched mRNA signatures and potentially reveal transcriptional heterogeneity in GBM tumors.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A microfluidic device, comprising:
    a microfluidic channel wherein an internal surface of at least one wall of the microfluidic channel comprises a plurality of grooves or ridges, or both grooves and ridges, arranged and configured to generate chaotic mixing within a fluid sample flowing through the microfluidic channel; and
    a plurality of elongate flexible linker molecules, each having a molecular weight between about 0.6-4.8 kDa, wherein each elongate flexible linker molecule is bound at a first end to an internal surface of at least one wall of the microfluidic channel and is bound at a second end to one or more binding moieties that specifically bind to a target extracellular vesicle.

2. The microfluidic device of claim 1, further comprising one or more layers of gelatin, wherein a first layer of the gelatin is bound to the internal surface of the microfluidic channel by physical adsorption or by binding to second members of the binding pair attached to the internal surface or attached to first members of the binding pair attached to the internal surface, and wherein an optional second layer of gelatin is bound to the first layer via a plurality of second members of the binding pair that are associated with the first members of the binding pair on both the first and the second layers of gelatin; and optionally, one or more subsequent layers of gelatin, each bound to a previous layer by the second members of the binding pair.

3. The microfluidic device of claim 2, wherein the elongate flexible linker molecules comprise at a first end thereof a binding moiety that binds to a surface layer of the gelatin, thus indirectly binding the elongate flexible linker molecules to the internal surface of the wall via the one or more layers of gelatin.

4. The microfluidic device of claim 1, further comprising a plurality of nanostructures, wherein the nanostructures comprise one or more binding moieties that bind to the internal surface of at least one wall of the microfluidic channel, and wherein the elongate flexible linker molecules are indirectly bound to the internal surface of the wall by an interaction of the first end of the plurality of elongate flexible linker molecules with the nanostructures bound to the internal surface.

5. The microfluidic device of claim 2, further comprising a plurality of nanostructures, wherein the nanostructures comprise one or more binding moieties that bind to a surface layer of the gelatin, and wherein the elongate flexible linker molecules are indirectly bound to the internal surface of the wall by an interaction of the first end of the plurality of elongate flexible linker molecules with the nanostructures bound to the surface layer of gelatin.

6. The microfluidic device of claim 2, further comprising a plurality of nanostructures, wherein the nanostructures are bound to a surface layer of gelatin by the second members of the binding pair that are associated with the first members of the binding pair, and wherein the elongate flexible linker molecules are indirectly bound to the internal surface of the wall by an interaction of the first end of the plurality of elongate flexible linker molecules with the nanostructures bound to the surface layer of gelatin.

7. The microfluidic device of claim 2, wherein the plurality of layers of gelatin comprises at least:
 a first layer of gelatin bound to the internal surface of at least one wall of the microfluidic channel; and
 a second layer of gelatin bound to the first layer of gelatin via the second members of the binding pair.

8. The microfluidic device of claim 1, wherein the plurality of elongate flexible linker molecules comprise polyethylene glycol (PEG).

9. The microfluidic device of claim 1, wherein the plurality of elongate flexible linker molecules comprise dextran.

10. The microfluidic device of claim 1, wherein the one or more binding moieties comprise at least one of antibodies, aptamers, lectins, heparin, glycoproteins, or deoxyribonucleic (DNA) fragments.

11. The microfluidic device of claim 1, wherein the one or more binding moieties specifically bind to at least one of an epidermal growth factor receptor (EGFR), podoplanin, barrier-to-autointegration factor (BAF), platelet-derived growth factor receptor (PDGFR), and ephrin receptor A2 (EphA2).

12. The microfluidic device of claim 1, wherein the binding moieties specifically bind to tumor-derived extracellular vesicles.

13. The microfluidic device of claim 1, wherein the plurality of grooves or ridges comprises two or more V-shaped grooves that are each defined in the at least one wall of the microfluidic channel; wherein each V-shaped groove comprises an apex and two arms connected to the apex to form the V-shape; and the two or more V-shaped grooves each comprise a first V-shaped groove that is orientated such that the apex of the first V-shaped groove points in the direction of flow through the microchannel, and a second V-shaped groove that is oriented such that the apex of the second V-shaped groove points against the direction of flow through the microchannel.

14. The device of claim 1, wherein each elongate flexible linker molecule has a molecular weight between about 1.8-4.0 kDa.

15. The device of claim 1, wherein each elongate flexible linker molecule has a molecular weight between about 2.0-3.0 kDa.

16. The device of claim 1, wherein each elongate flexible linker molecule has a molecular weight of about 2.0 kDa.

* * * * *

UNITED STATES PATENT AND TRADEMARK OFFICE
CERTIFICATE OF CORRECTION

PATENT NO. : 11,548,002 B2
APPLICATION NO. : 16/613710
DATED : January 10, 2023
INVENTOR(S) : Eduardo Reategui, Shannon Stott and Mehmet Toner Page 1 of 1

It is certified that error appears in the above-identified patent and that said Letters Patent is hereby corrected as shown below:

In the Claims

Column 32, Claim 2, Line 48:
Delete "the" and insert -- a --

Signed and Sealed this
Fourth Day of July, 2023

Katherine Kelly Vidal
*Director of the United States Patent and Trademark Office*